United States Patent [19]

Muller et al.

[11] Patent Number: 5,952,390
[45] Date of Patent: Sep. 14, 1999

[54] 10-SUBSTITUTED 1,8-DIHYDROXY-9(10H) ANTHRACENONE PHARMACEUTICALS

[75] Inventors: Klaus Muller, Münster; Wolfgang Weigrebe, Zeirlarn; Hans Reindl, Hirschau, all of Germany

[73] Assignee: Teva Pharmaceutical Industries Ltd., Petah Tiqva, Israel

[21] Appl. No.: 09/075,314

[22] Filed: May 8, 1998

Related U.S. Application Data

[60] Continuation-in-part of application No. 08/825,075, Mar. 27, 1997, Pat. No. 5,844,004, which is a division of application No. 08/400,209, Mar. 7, 1995, Pat. No. 5,661,187, which is a continuation of application No. 08/092,854, Jul. 19, 1993, Pat. No. 5,426,197.

[51] Int. Cl.$^6$ .................................................. A61K 31/12
[52] U.S. Cl. ............................................. 514/680; 552/290
[58] Field of Search ............................. 514/680; 552/290

[56] References Cited

U.S. PATENT DOCUMENTS 5,661,187   8/1997   Muller et al. .......................... 515/680

*Primary Examiner*—James H. Reamer
*Attorney, Agent, or Firm*—Kenyon & Kenyon

[57] ABSTRACT

Therapeutic compositions comprising 1,8-dihydoxy-10-[2-(4-methylphenyl)-1-oxoethyl]-9(10H)-anthracenone and (R,S)-1,8-dihydroxy-10-(1-oxo-4-phenylpentyl)-9(10H)-anthracenone, said compounds having substantial therapeutic activity and minimal inflammatory effect.

10 Claims, 2 Drawing Sheets

10-SUBSTITUTED 1,8-DIHYDROXY-9(10H) ANTHRACENONE PHARMACEUTICALS

This is a CIP of Ser. No. 08/825,075, filed Mar. 27, 1997 now U.S. Pat. No. 5,844,004, which is a division of Ser. No. 08/400,209, filed Mar. 7, 1995, now U.S. Pat. No. 5,661,187 issued Aug. 26, 1997 which is a continuation of Ser. No. 08/092,854 filed Jul. 19, 1993 now U.S. Pat. No. 5,426,197 issued Jun. 20, 1995.

FIELD OF THE INVENTION

This invention relates to anthracenone compounds useful in the treatment of allergic and inflammatory conditions and therapeutic compositions containing such compounds. The invention relates also to the provision of therapeutic compositions effective at low dose with low irritancy.

REPORTED DEVELOPMENTS

Inflammation in the body occurs in response to numerous conditions including, but not limited to, physical injury, allergy, tumor growth, certain disease states, chemical damage, and bacterial, parasitic or viral infection. Typically, inflammation results in both local and systemic effects. Representative of local effects that can occur are increased vascular permeability, release of degradative enzymes, migration to the affected site by leukocyte cells, neutrophil burst response to destroy invading cells, and the secretion of cytokines. There is considerable interest in the provision of therapeutic compositions containing new compounds that are capable of controlling inflammation in the body.

An example of an inflammatory condition (disease) is psoriasis—a widespread, chronic, inflammatory and scaling skin disease, chiefly characterized by increased cell proliferation of the epidermis. Typically hyperproliferation alone is not sufficient to produce a psoriatic lesion, an inflammatory component also being an important part of the disease process, Fry, L., Br. J. Dermatol., 119, 445–461 (1988).

Psoriasis is known to be associated with numerous biochemical abnormalities. Lowe, N., Drug Dev. Res., 13, 147–155 (1988). One biochemical characteristic of psoriatic skin is the presence of oxygenation products of arachidonic acid in elevated concentrations. In particular, evidence has been provided showing the enhanced production of lipoxygenase (LO) products such as leukotriene $B_4$ ($LTB_4$) and 5-hydroxyeicosa-tetraenoic acid (5-HETE). Additionally, the effects of lipoxygenase (LO) products in the skin correlate with several pathological features of psoriasis, in particular, leukocyte migration and enhanced cell proliferation.

Correlations have been demonstrated between the effects of certain antipsoriatic drugs and their effects on lipoxygenase enzymes. Accordingly, regulation of lipoxygenase pathways is an important target for therapeutic intervention in the treatment of psoriasis, and also for other inflammatory conditions or allergic conditions. See, for example, Jones, G. H. et al., J. Med. Chem., 29, 1504–1511 (1986), and Venuti, M. C. et al., J. Med. Chem., 31, 2132–2136 (1988).

Anthralin (1,8-dihydroxy-9(10H)-anthracenone) also referred to as "dithranol" is probably the most commonly used topical agent for the treatment of psoriasis. However, anthralin therapy causes several unpleasant side effects. For example, non-affected skin surrounding a psoriatic lesion to which anthralin is applied is frequently irritated. Additional side effects at the site of application (representative of a condition of inflammation or irritancy) are known to include erythema, inflammatory edema, and also elevation in skin temperature.

With respect to the activity and also the side effects of anthralin, substantial evidence suggests that free radicals (Finnen, M. J., Lancet II, 1129–1130 (1984), Shroot, B. et al., Arzneim.-Forsch./Drug Res., 36, 1253–1255 (1986)), and also active oxygen species (Muller, K. et al., Arch. Pharm. (Weinheim), 320, 59–66 (1987), Muller, K. and H. Kappus, Biochem. Pharmacol., 37, 4277–4280 (1988), Muller, K. et al., Photochem. Photobiol., 52, 445–450 (1990), Muller, K. et al., Arzneim.-Forsch/Drug Res., 41, 1176–1181 (1991)) are involved.

In connection with determining the structural features of anthralin that confer therapeutic activity, P. G. Unna, investigated several anthracenone derivatives and found that anthralin and also 1-hydroxy-9(10H)-anthracenone were effective in the treatment of psoriasis, Dermatol. Wochenschr., 62, 116–137 (1916). The latter compound was stated to be a minimum structure for antipsoriatic activity. Although there have been attempts to develop new therapeutically effective derivatives of anthralin, for which initial reports were promising, later reports have indicated that these compounds were less effective and more irritating than anthralin itself (Kammerau, B. et al., "Absolute Concentrations of Dithranol and Triacetyl-Dithranol in the Skin Layers After Local Treatment: In Vivo Investigations with Four Different Types of Pharmaceutical Vehicles", J. Invest. Dermatol., 64, 145–149 (1975), and Greaves, M. W., "Irritation and Staining by 10-Butyryl-Dithranol (Butantrone)", Int. J. Clin. Pharm. Res., 6, 315–316 (1986)).

Butantrone as introduced in 1980 by Mustakallio, (Mustakallio, K. K. et al., "1,8-Dihydroxy-10-Acyl-9-Anthrones with Anti-Psoriasis Properties, Finland Patent 57743 (CI C07C49/747)", Chem. Abstr., 1980, 93, P 204348z) is a C-10-butyryl derivative of anthralin that is not cleaved to form anthralin. When applied therapeutically, this compound commonly elicits a widespread and delayed irritation effect. Additional alkylacyl derivatives are described in published European Patent Specification Number 0 017 420 A1 filed on Mar. 25, 1980 bearing application number 80300928.1.

Additional references wherein are disclosed anthralin derivatives having anti-inflammatory (or anti-psoriatic) activity include Tanzer, H. et al., Arch. Pharm., 324, 841–846 (1991); U.S. Pat. No. 4,299,846 to Mustakallio et al.; and numerous U.S. Patents to Schroot et al. (for example, U.S. Pat. Nos. 4,677,123, 4,558,069, 4,464,301, 4,568,743, 4,755,530, 4,826,996, and 4,997,961).

Accordingly, there is a clear need for improved anti-inflammatory agents (including, for example, anti-psoriatic agents) that are effective at a low dose thereof, thereby avoiding irritancy and/or other complications associated with doses (including the typically higher doses) associated with administration of prior art anthracenone compounds.

SUMMARY OF THE INVENTION

The present invention is directed to novel 10-substituted 1,8-dihydroxy-9-(10H) anthracenone compounds, and analogs thereof, having therapeutic utility with respect to allergic or inflammatory conditions. In particular, numerous of the improved anthracenone compounds provided for according to the practice of the invention are effective at low concentrations thereof to treat patients for allergic or inflammatory conditions, thereby avoiding the undesirable allergic or inflammatory effects caused, in whole or in part, by typical concentrations of radicals or active oxygen species that are produced from anthracenone compounds.

Accordingly, there is provided an anthracenone compound according to formula I, as defined below, said compound containing a substituent (X), and optionally, one or more substituents (R).

There is provided also an anthracenone compound according to formula II as defined below, said compound containing, optionally, a substituent (n) and/or, optionally, one or more substituents (R). Additionally, there are provided compounds which are functional analogs of the formula I and formula II compounds.

As aforementioned, therapeutic compositions of the invention are effective at doses thereof that substantially avoid the adverse inflammatory or irritancy effects normally associated with the use of 1,8-dihydroxy-9(10H)-anthracenone and related compounds.

Representative of allergic or inflammatory conditions (diseases) that may be treated according to the practice of the invention are rheumatoid arthritis, osteoarthritis, multiple sclerosis, allergic rhinitis, asthma, psoriasis, eczema, seborrhea, contact dermatitis, sunburn and inflammatory diseases of the digestive tract such as ulcerative colitis. Additionally, the compounds of the invention have anti-proliferative effects and anti-neoplastic effects.

Accordingly, there is provided also a 10-substituted 1,8-dihydroxy-9(10H)-anthracenone compound wherein the arylacyl C-10 blocking moiety thereof is stable to metabolic degradation, said compound being capable of inhibiting lipoxygenase activity in a patient when provided in the form of a therapeutic composition, said inhibitory activity thereof not made ineffective by an inflammatory effect caused by said compound. Additionally there is provided a related compound wherein the phenylalkylidene C-10 blocking moiety thereof is stable to metabolic degradation, said compound being capable of inhibiting lipoxygenase activity in a patient when provided in the form of a therapeutic composition, said inhibitory activity thereof not made ineffective by an inflammatory effect caused by said compound.

Additionally, in a method of treating a patient for an allergic or inflammatory condition with a 9-anthracenone compound wherein contacting said patient with said compound results in a further allergic or inflammatory effect caused, in whole or in part, by radicals or active oxygen species the production thereof involving participation of the C-10 position of said compound, the invention provides for the improvement of providing said compound with a C-10 blocking moiety consisting essentially of a non-phenolic arylacyl group or a non-phenolic phenylalkylidene group.

In connection with the discovery that the redox activity of certain of the compounds of the invention can be adjusted to increase the therapeutic activity thereof, there is provided in a method of treating a patient for an allergic or inflammatory condition with a 9-anthracenone compound containing a C-10 blocking moiety, said moiety consisting essentially of an arylacyl or phenylalkylidene group, wherein contacting a tissue of said patient with said compound results in both inhibition of lipoxygenase activity and also allergy or inflammation at predetermined levels thereof, the improvement comprising modifying said compound, prior to treatment therewith, to contain said C-10 blocking moiety as a phenolic form thereof, said resultant compound having greater therapeutic lipoxygenase inhibitory activity than said predetermined level thereof, said increased inhibitory activity not made ineffective by an allergic or inflammatory effect of said modified compound whether said effect is greater or less than said predetermined value thereof.

Additionally, there are provided also methods of treating inflammatory conditions such as psoriasis and contact dermatitis.

Further additional and representative aspects of the invention are described below according to the following detailed description of the invention.

DETAILED DESCRIPTION OF THE INVENTION

Figure 1:
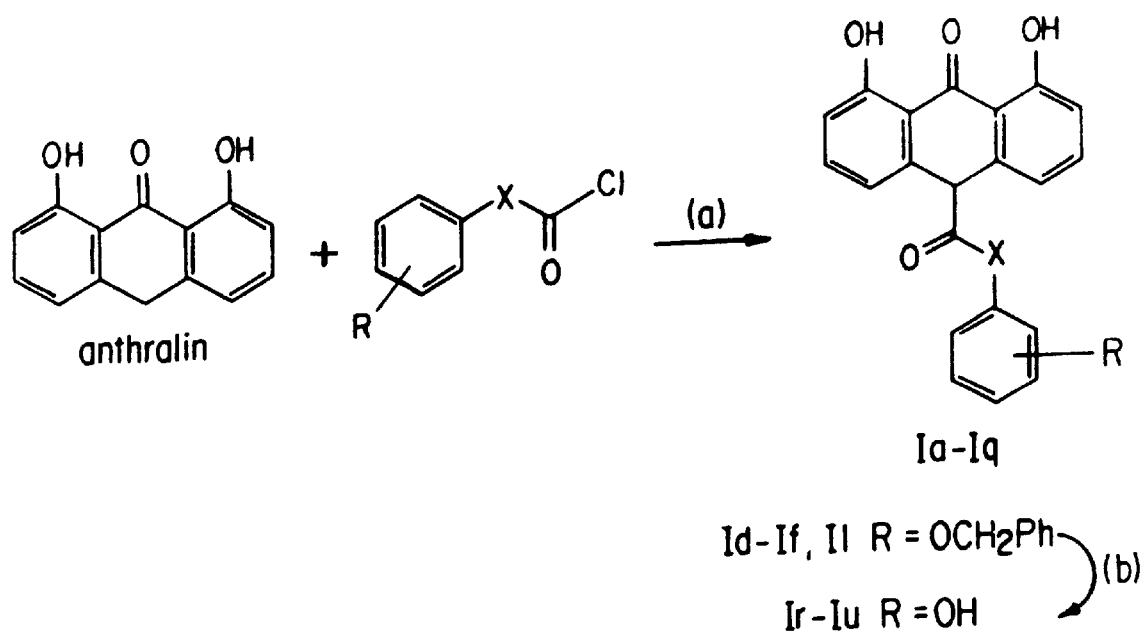
FIG. 1 depicts a representative reaction scheme suitable for the production of 10-arylacyl-9-anthracenone compounds of the invention.

Information Concerning the Structure of 10-Substituted 1,8-dihydroxy-9(10H)-anthracenones of the Invention As set forth above, the compounds of the invention represent 10-arylacyl or 10-phenylalkylidene substituted 1,8-dihydroxy-9(10H)-anthracenones, or analogs thereof.

According to the practice of the invention, there are provided 10-arylacyl compounds according to formula I,

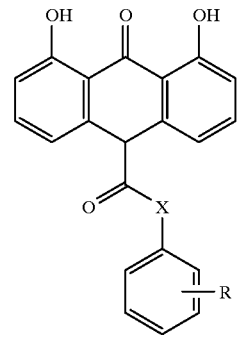

[formula I]

wherein said compound contains a substituent (X) and, optionally, one or more substituents (R). Preferred compounds according to the practice of the invention include those described in Table I below.

Aerobic animal life is dependent upon the capability of metabolizing chemical compounds oxidatively, for example, with oxygen. Metabolism of oxygen is, however, associated with the unavoidable production of oxygen-derived toxic compounds including radicals and active oxygen species (for example, the oxygen anion radical $O_2^-$, OH•radical, hydrogen peroxide and an excited state species, singlet molecular oxygen. Accordingly, close regulation over the fate of such substances, toxic to aerobic animal life, is necessary.

In humans, the controlled release of oxygen-derived free radicals by specialized immune system-related cells per-forms an antibacterial killing role. See, for example, Del Maestro, R. F., *Free Radicals in Molecular Biology, Aging, and Disease*, D. Armstrong et al., eds., Raven Press, New York, N.Y., at 87–102 (1984). However, the presence of or improper regulation of free radical species is associated with numerous disease states (See, for example, R. F. Del Maestro at page 91 thereof), and the prerequisites for free radical injury are normally fulfilled during inflammatory processes. The inflammatory reaction to injury or infection is defined by a wide variety of cellular responses and chemical (biochemical) reactions. Of importance in the creation and maintenance of an inflammatory state is the production of free radicals and also active oxygen species including free radicals derived therefrom. For a review of these phenomena, see for example, Rainsford, K. D. and Swann, B. P., "The Biochemistry and Pharmacology of Oxygen Radical Involvement in Eicosanoid Production" *in The Biology and Chemistry of Active Oxygen*, J. V. Bannister et al., eds., Chapter 5, Elsevier, New York, N.Y. (1984).

Of importance also to the existence of inflammatory state in a patient is the metabolism of arachidonic acid, itself a precursor or many biologically important compounds, for example, eicosanoids, prostaglandins, leukotrienes ($LTB_4$, $LTC_4$, $LTD_4$, and for example, $LTE_4$) and peptidoleukotrienes, through which an inflammatory condition is mediated. The present invention pertains in part to the regulation of abnormal arachidonic acid metabolism for the relief of inflammatory or allergic conditions.

As described hereinbelow there are provided two functional classes of anti-inflammatory 1,8-dihydroxy-9(10H) anthracenone compounds.

Without being limited as to theory, such compounds, whether containing a 10-arylacyl or 10-phenylalkylidene moiety, may be defined broadly as "redox" and "non-redox" compounds based upon the mechanism whereby they inhibit 5-lipoxygenase, an enzyme that mediates the inflammatory process. "Redox" compounds are typically capable, at a reasonable molecular distance of donating an electric charge to $Fe^{+3}$ of lipoxygenase thereby inactivating it, whereas "non-redox" compounds exert more specific effects and typically at close range.

Although the compounds of the invention are defined, in part, according to this parameter, and that the structure of further therapeutic compounds may be predicted thereby, it is understood that this is but one mechanism whereby the compounds of the invention are therapeutically active.

Numerous studies suggest that both the therapeutic modes of action of anthracenone compounds and also the mechanisms of irritancy involve free radicals and active oxygen species. Thus, it has been difficult to separate beneficial effects from adverse side effects in the design of such compounds. Accordingly, a principal additional characteristic of numerous of the compounds of the invention is that therapeutic effects may be derived therefrom at concentrations of such substances for which inflammatory side effects (such as irritancy) are minimized.

Preferably the 10-arylacyl moieties of the non-redox compounds of the invention are not so large as to prevent interaction by the compound with 5-lipoxygenase, or with other enzymes that mediate the inflammatory process. In this regard, most preferred are structures wherein X in formula I is preferably no greater than about 3 carbons in length and the optionally present R of formula I is no greater in size than phenylmethoxy, the R structure of compound Id.

In connection with designs for suitable arylacyl structures to be located at position 10 of the therapeutic compound, it is noted that such structures are, in general, subject only to slower metabolic degradation than prior art alkylacyl structures. Additionally, in all such structures formation of free radicals at C-10 thereof is maintained, preserving therapeutic effect. In this regard, see, for example, K. Müller, *Archiv der Pharmazie*, 321, 385–389 (1988).

Representative of the considerable achievement of the present invention, reference to Table I shows that compound Ip is nearly 100 times more effective than anthralin (Table I, supplement) as an inhibitor of lipoxygenase. Without being limited as to theory, it is suggested that any loss in potentially therapeutic radical formation capability caused by substitution of a single arylacyl group at C-10 is compensated for by high specificity of interaction with a target enzyme site.

With respect to redox-active compounds according to formula I, it is recognized that such compounds can donate an electron (converting lipoxygenase $Fe^{+3}$ into inactive $Fe^{+2}$) over considerable interatomic distance. Accordingly, selection of one or more substituents R to act as electron donating agents in such compounds according to the practice of the invention includes use of, for example, representative groups such as bromo, iodo, amino, hydroxy, fluoro, mercapto, substituted mercapto, substituted amino, aryloxy and arylmethoxy, with moieties such as 3,4,5-trihydroxy and 3,4,5-triamino being among the most preferred.

Representative of those compounds (including redox and non-redox) most preferred according to the practice of the invention is a compound selected from the group consisting of: 1,8-Dihydroxy-10-[2-(4-methoxyphenyl)-1-oxoethyl]-9(10H)-anthracenone (Ic); 1,8-Dihydroxy-10-[1-oxo-2-(4-phenylmethoxyphenyl)ethyl]-9(10H)-anthracenone (Id); 1,8-Dihydroxy-10-(1-oxo-3-phenylpropyl)-9(10H)-anthracenone (Ih); 1,8-Dihydroxy-10-(3-(4-methoxyphenyl)-1-oxopropyl)-9(10H)-anthracenone (Ii); 1,8-Dihydroxy-10-(1-oxo-4-phenylbutyl)-9(10H)-anthracenone (Ip); 1,8-Dihydroxy-10-(1-oxo-5-phenylpentyl)-9(10H)-anthracenone (Iq); and 1,8-Dihydroxy-10-[2-(3,4,5-trihydroxyphenyl)-1-oxoethyl]-9(10H)-anthracenone (It).

With respect to the phenylalkylidene compounds according to formula II, similar considerations apply in connection with selecting an optional substituent (n) and/or, optionally, one or more substituents (R).

According to the practice of the invention, there are also provided 10-phenylalkylidene compounds according to formula II,

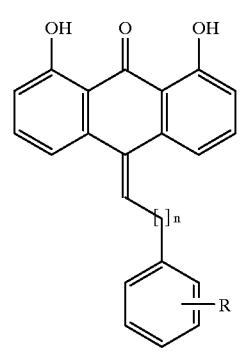

[formula II]

wherein said compound containing optionally a substituent (n) and/or, optionally, one or more substituents (R).

Compounds that are capable of functioning as high specific activity redox inhibitors of 5-lipoxygenase are prepared by substituting the phenyl ring with electron donor groups, for example, 3,4,5-trihydroxy or any of the other groups as mentioned above. This effect is expected to be particularly dramatic if (n) in said structure is zero, thereby permitting effective donation of an electron to (through) C-10.

Representative of those compounds most preferred according to the practice of the invention is a compound selected from the group consisting of: 1,8-Dihydroxy-10-[(4-nitrophenyl)methylen]-9(10H)-anthracenone (IId); 1,8-Dihydroxy-10-[(3-phenylpropyliden)methylen]-9(10H)-anthracenone (IIj); 1,8-Dihydroxy-10-[(4-hydroxyphenyl)methylen]-9(10H)-anthracenone (IIp); 1,8-Dihydroxy-10-[(3,4-dihydroxyphenyl)methylen]-9(10H)-anthracenone (IIq); and 1,8-Dihydroxy-10-[(3,4,5-trihydroxyphenyl)methylen]-9(10H)-anthracenone (IIr).

Consistent with the practice of the invention, the arylacyl or phenylalkylidene C-10 moiety as described can be replaced (modified) with a moiety containing a terminal heterocyclic group such as pyrrole or imidazole, as long as the electron donating or, for example, C-10 radical stabilizing capability of the compound is maintained. Additionally, pyrrole and imidazole are particularly useful as C-10 blocking moieties in that they can potentially interact with iron centers such as of 5-lipoxygenase, thereby inactivating them and minimizing inflammatory response.

As aforementioned, a principal advantage of the therapeutic compounds of the invention is that they may be provided in or on the body of a patient at a concentration thereof that provides for therapeutic effects, such as inhibiting lipoxygenase activity or other inflammatory processes, and wherein side effects such as irritancy or inflammation caused by said compounds are insufficient to make ineffective the therapeutic dose thereof. In connection herewith it is understood that "patient" includes a human patient, and as expected, a veterinary patient.

An additional advantage of the compounds of the present invention is that they are stable to metabolic degradation, particularly in comparison to certain prior art alkylacyl 10-substituted 9-anthracenones.

In connection with confirming the resistance to metabolic degradation of the compounds of the invention, the following procedures will be of interest. C-10-acylated compounds of Tanzer et al., *Arch. Pharm.*, 322, 441–444 (1989) were determined to be stable at pH 7.5 when incubated for glucose-6-phosphate dehydrogenase inhibition assays. Under these conditions, anthralin itself was degraded almost completely. The compounds of the present invention are stable at pH 7.4 (in phosphate buffer) when incubated for the lipoxygenase assay. Under these conditions, anthralin was degraded within 2 hours. Additionally of note, skin homogenates of NMRI-mice did not cleave the C-10-C=O (double bond) in C-10 acyl derivatives (Tanzer, H. et al., *Arch. Pharm.*, 324, 841–846 (1991), at page 844 thereof) while ester linkages were cleaved hydrolytically. These procedures are expected to be useful in confirming the metabolic stability of the compounds of the invention.

Clinical Indications Subject to Treatment According to the Practice of the Invention The following conditions are selected for description herein as being representative of inflammatory, allergic, or neoplastic conditions that are suitable for treatment according to the practice of the invention. As is recognized in the art, and in relation to psoriasis, they are linked by underlying concepts of inflammation and/or free radical mechanisms.

Arthritic Disease

Rheumatoid arthritis is a chronic inflammatory disease primarily of the joints that may result in permanent loss of joint function. Irreversible loss of joint function is attributed to severe degradation of collagen and degradation also of bone, ligament and tendon. Associated chronic inflammation results in part from immune response at the affected joint, although the exact nature of the triggering antigens is unknown. The immune response may be autoimmune in origin. Mullins, D. E. and Rohrlich, S. T. *Biochemica et Biophysica Acta*, 695, 177–214 (1983) at 192–193 thereof describe the etiology of the disease in detail. Briefly there is a progressive loss of cartilage (a connective tissue) caused by invading cells. Both collagen and proteoglycan components of the cartilage are degraded by enzymes released at the affected site.

Anti-neoplastic Effect

The therapeutic compositions of the invention may be used in the treatment of a wide variety of cancers such as carcinomas, sarcomas, melanomas and lymphomas and which may affect a wide variety of organs, including, for example, the lungs, mammary tissue, prostate gland, small or large intestine, liver, heart, skin, pancreas and brain. The therapeutic compositions may be administered to patients in the case of treatment of tumors, for example, by injection (intravenously, intralesionally, peritoneally, subcutaneously), or by topical application and the like as would be suggested according to the routine practice of the art.

Therapeutic Compositions and Administration Thereof

The amount of 10-substituted arylacyl or phenylalkylidene substituted 1,8-dihydroxy-9(10H) anthracenone (or analog thereof) to administer for the prevention or inhibition of an inflammatory or allergic condition, or as to act as an anti-proliferative or anti-neoplastic agent, can be determined readily for any particular patient according to recognized procedures. Representative of suitable quantities of the compounds of the invention (to be mixed, optionally, with pharmaceutically acceptable carriers) include, for example, from about 10 to 100 milligrams for oral administration, from about 10 to 100 milligrams for injection, from about 10 to 500 milligrams for a suppository, and from about 0.1% to about 5.0% by weight of a topically applied product such as ointment, cream, gel, aerosol, or liquid. Precise dosing for a patient can be determined according to routine medical practice for each of the particular compounds of the invention taking into consideration the level of therapeutic activity and the level of irritancy associated with each milligram thereof.

Additional information useful in the selection of therapeutic compositions is provided as follows. For use in the treatment of inflammatory or degenerative conditions, as those terms are recognized in the art, the therapeutic compositions may be administered, for example, by injection at the affected site, by aerosol inhalation (as in the case of emphysema or pneumonia), or by topical application or transdermal absorption as would also be suggested according to the routine practice of the art.

As described above, the 10-substituted-9-anthracenones of the invention (or analogs thereof) may be incorporated into pharmaceutically-acceptable carriers for application (directly or indirectly) to the affected area. The nature of the carrier may vary widely and will depend on the intended location of application and other factors well known in the art. Such carriers of anthralin or anthracenone compounds are well known in the art. See, for example, Kammerau, B. et al., *J. Investigative Dermatology*, 64, 145–149 (1975). For example, for application to the skin, a cream or ointment base is usually preferred, suitable bases including lanolin, and the like.

For topical administration, the compositions of the present invention can be provided in those pharmaceutical forms in which the compound is applied externally by direct contact with the skin surface. Conventional pharmaceutical forms for this purpose include ointments, unguents, tinctures, solutions, creams, lotions, pastes, jellies, sprays, aerosols, bath oils, shampoos, suspensions, micronized powders, and the like, using typical bases such as petrolatum, lanolin, polyethylene glycols and alcohols. These compositions can also contain additional inert or pharmacologically active adjuvants such as binders, fillers, diluents, thickening agents, preservatives and the like. Certain compositions of this invention may preferably include skin penetrating adjuvants such as, for example, dimethyl sulfoxide, dimethyl acetamide, and so forth.

The pharmaceutical compositions of this invention can be administered enterally, for example, in the form of tablets, granules, gels, capsules, syrups, drinkable suspensions, ingestible powders, or even in the form of injectable solution or suspensions.

The pharmaceutical compositions can also be injected, either intravenously, intramuscularly, intradermally, intra- or peri-lesionally, or subcutaneously using, for example, appropriate sterile saline compositions.

The pharmaceutical compositions may also be applied rectally by suppositories, sublingually, transdermally, and so forth.

An additional method whereby the therapeutic compositions of the invention can be formulated comprises incorporation thereof into the lumen of liposomes.

If desired, the therapeutic compositions of the invention can be incorporated into bandages and other wound dressings to provide for continuous exposure of the wound to the therapeutic molecules. Aerosol applications are also useful. Additionally, the compositions can be applied topically to the affected area, typically as creams, ointments or lotions to the skin. On the skin, it is desirable to continually maintain the treatment composition on the affected area during healing, with several applications of the treatment composition per day being preferred usually.

Additionally, it is within the practice of the invention to provide to a patient at a site of treatment therein a therapeutic composition containing one or more compounds of the invention and one or more additional therapeutic substances.

Preparation of the Compounds of the Invention

Methods whereby the compounds of the invention are synthesized (and their structures confirmed) are described below in Examples 6 and 7.

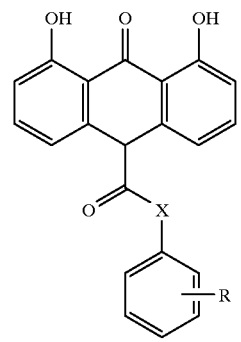

TABLE I

Redox Properties of and 5-LO inhibition in Bovine
PMNL by 10-Phenylacyl-substituted 1,8-Dihydroxy-9(10H)-anthracenones

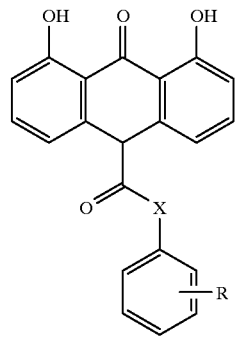

TABLE II

Redox Properties of and 5-LO inhibition in Bovine
PMNL by 10-Phenylalkylidene-substituted 1,8-Dihydroxy-9(10H)-anthracenones

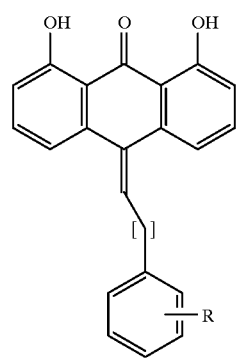

[a]Inhibition of 5-HETE and LTB$_4$ biosynthesis in bovine PMNL; n = 3 or more; standard errors average 10% of the indicated values; values in parentheses are percent inhibition at the indicated concentrations ($\mu$M).
[b]Reducing activity against 2,2-diphenyl-1-picrylhydrazyl with equimolar amount of test compound.
[c]Not reactive; $k_{DPPH} < 1 \, M^{-1}s^{-1}$.
[d]Highly reactive (approximate values).
[e]Deoxyribose damaging property as a measure of hydroxyl radical formation; indicated values are $\mu$mol malondialdehyde/mmol deoxyribose (controls: 8.3 ± 1.2).
[f]Inhibition of lipid peroxidation in bovine brain phospholipic liposornes; n = 3 or more; standard errors average 20% of the indicated values.
[g]not determined.

TABLE III

Chemical Data of 10-Phenylacyl-substituted 1,8-Dihydraxy-9(10H)-anthracenones.

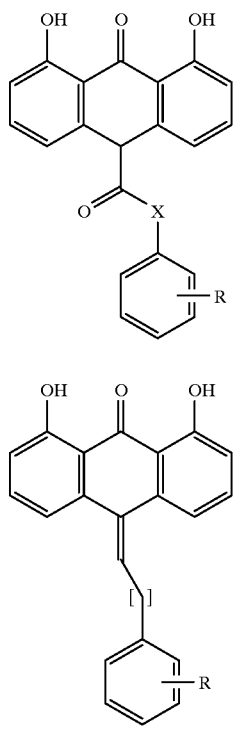

[a]Decomposition.
[b]E = ether; EA = ethyl acetate; H = hexane M = methanol; MC = methylene chloride; P = petroleum ether (40–60° C.).
[c]Elemental analyses were within ± 0.4% of calculated values.
[d]not determined.

TABLE I (Addendum)

Redox Properties of and 5-LO Inhibition in Bovine PMNL by Anthralin and Butantrone.

| | 5-LO $IC_{50} \mu M^a$ | $k_{DPPH}$ $[M^{-1}s^{-1}]^b$ | deoxyribose degradation ($\mu$mol MDA/ mmol) $X^e$ | LPO $IC_{50} \mu M^f$ |
|---|---|---|---|---|
| Anthralin | 37 | 24.2 ± 4.2 | 2.89 ± 0.14 | 12 |
| Butantrone | (38% at 30) | 7.0 ± 0.6 | 0.24 ± 0.03 | 4 |

[a]Inhibition of 5-HETE and $LTB_4$ biosynthesis in bovine PMNL; n = 3 or more; standard errors average 10% of the indicated values; values in parentheses are percent inhibition at the indicated concentrations ($\mu$M).
[b]Reducing activity against 2,2-diphenyl-1-picrylhydrazyl with equimolar amount of test compound.
[c]Not reactive; $k_{DPPH} < 1\ M^{-1}s^{-1}$.
[d]Highly reactive (approximate values).
[e]Deoxyribose damaging property as a measure of hydroxyl radical formation; indicated values are $\mu$mol malondialdehyde/mmol deoxyribose (controls: <0.1).
[f]Inhibition of lipid peroxidation in bovine brain phospholipid liposomes; n = 3 or more; standard errors average 20% of the indicated values.
[g]Not determined.

EXAMPLES

The following examples are representative of the practice of the invention.

EXAMPLE 1
Application of Anthracenones to Arthritis-Affected Tissues

In vivo model systems are presently available to investigate arthritic disease states. For example, it has been demonstrated that Wistar rats, when immunized with native type II collagen (isolated from digestion of fetal bovine articular cartilage), develop arthritic disease as a result of collagen-immunity response. Such response is believed to be related to the progression of human rheumatoid arthritis. See Stuart, J. M. et al. *J. Exp. Med.*, 155, 1–16 (1982) and references cited therein. Other animal models include use of intradermal injection with complete Freunds adjuvant (see Chang et al. *Arth. Rheum.*, 23, 62–71 (1980)) and intraperitoneal injection of Streptococcus cell wall extracts in Lewis rats (see Wilder, et al. *Arth. Rheum.*, 25, 1064 (1982)).

The results of model studies and the discoveries of the present invention suggest that progression of arthritic disease in humans may be halted, or in fact reversed, using subcutaneous or intraarticular injections of the compounds of the invention, at about up to 5 $\mu$g/ml or higher using an injection volume compatible with the volume of the affected site, for example, about 0.1 ml per 10 ml of inflamed synovial fluid, said administration being made on a daily basis for a period of about 1 to about 30 days.

It is expected that improvement will be demonstrated within this period following such daily administrations at which time the injections may be discontinued. If further healing does not occur, a second course of administrations would be indicated.

EXAMPLE 2
Determination of Reducing Activity of Test Compound Toward 2,2-Diphenyl-1-picrythydrazyl (DPPH)

This assay followed generally the procedures of Blois, M. S., "Antioxidant Determinations by the Use of a Stable Free Radical", *Nature*, 181, 1199–1200 (1958) and Kato, K. et al., "Studies on Scavengers of Active Oxygen Species. 1. Synthesis and Biological Activity of 2-O-Alkylascorbic Acids", *J. Med. Chem.*, 31, 793–798 (1988). In time studies, 1 ml of test compound solution ($10^{-4}$M) was added to 1 ml of DPPH solution ($10^{-4}$M), each in acetone/PBS (1+1 V/V), and the reduction of DPPH was followed spectrophotometrically at 516 nm. Plots of the reciprocal of DPPH concentrations against time gave straight lines, and the second-order rate constants were obtained from the slopes and are expressed as mean values (n=3–6). In the cases where DPPH was very fast approximate values are given and expressed as $k_{DPPH} > 100$ or $k_{DPPH} >> 100 M^{-1}s^{-1}$.

Since conversion of arachidonic acid into $LTB_4$ by 5-LO is a radical based oxidation, it is not surprising that most 5-LO inhibitors possess redox properties and can be considered as antioxidants/free radical scavengers. These compounds inhibit 5-LO by donating an electron during enzyme catalysis. Because a radical scavenging antioxidant reacts rapidly with the stable free radical 2,2-diphenyl-1-picrylhydrazyl (DPPH), Blois, M. S., "Antioxidant Determination by the Use of a Stable Free Radical", *Nature*, 181, 1199–1200 (1958); Kato, K. et al., "Studies on Scavengers of Active Oxygen Species. I. Synthesis and Biological Activity of 2-O-Alkylascorbic Acids", *J. Med. Chem.*, 31, 793–798 (1988), the reactivities of the new compounds with DPPH were determined by decrease in absorbance at 516 nm. Phenylacyl substitution at C-10 of anthralin substantially reduced redox activity compared to anthralin. However, substitution on the phenyl moiety of the side chain by two or three hydroxyl groups dramatically increased redox activity reflecting the reducing capability of the phenolic hydroxyl. Substitution of both C-10 hydrogen atoms of anthralin by phenylalkylidene groups nearly abolished reactivity with DPPH.

The results of these determinations for compounds Ia–Iu and IIa–IIr are given in Tables I and II.

EXAMPLE 3
Degradation of 2-Deoxy-D-ribose

This assay followed generally the procedures of Gutteridge, J. M. C., "Reactivity of Hydroxyl and Hydroxyl-Like Radicals Discriminated by Release of Thiobarbituric Acid-Reactive Material from Deoxy Sugars, Nucleosides and Benzoate", *Biochem. J.,* 224, 761–767 (1984) and of Laughton, M. J. et al., "Antioxidant and Prooxidant Actions of the Plant Phenolics Quercetin, Gossypol and Myricetin", *Biochem. Pharmacol.,* 38, 2859–2865 (1989). The following reagents were added to glass tubes in the order and at the final concentrations stated. 0.3 ml $KH_2PO_4$-KOH buffer, pH 7.4 (30 mM), 0.2 ml $H_2O$ bidist., 0.2 ml 2-deoxy-D-ribose (2 mM), 0.2 ml $FeCl_3 \cdot 6 H_2O$ (0.1 mM), 0.1 ml anthracenone derivative (75 $\mu$M). Stock solutions of the compounds were made up fresh before use. Appropriate blanks and controls with the vehicle (acetonitrile) were conducted. The final reaction volumes were standardized to 1.0 ml. The reaction mixtures were incubated for 2 h at 37° C. in a shaking water bath. 1.0 ml of 2.8% (w/v) trichloroacetic acid and 1.0 ml of 1% (w/v in 0.05 N NaOH) 2-thiobarbituric acid (TBA) were added, and the samples were heated at 100° C. for 15 min and then cooled in an ice bath (5 min). Then 2.0 ml of the reaction mixtures were treated with 0.05 ml of 36% (w/v) HCl and 2.0 ml of 1-butanol and the mixtures were vigorously shaken in a vortex mixer (Heidolph) for 15 s. The organic layer was separated by centrifugation at 3000 rpm (15 min) and the absorbance at 532 nm was measured against butanol. Calibration was performed using a malondialdehyde standard prepared by hydrolysis of 1,1,3,3,-tetraethoxypropane, Gutteridge, J. M. C., "The Use of Standards for Malondialdehyde", *Anal. Biochem.,* 1975, 69:518–526. TBA reactive material is expressed in terms of $\mu$mol MDA per mmol deoxyribose. The results of the above procedures for compounds Ia–Iu and IIa–IIr are given in Tables I and II.

EXAMPLE 4
Assay of Lipid Peroxidation in Bovine Brain Phospholipid Liposomes Phospholipids were prepared essentially as described by Gutteridge, J. M. C., "The Measurement of Malondialdehyde in Peroxidised Ox-Brain Phospholipid Liposomes", *Anal. Biochem.,* 82, 76–82 (1977). Bovine brain, cooled on ice, was freed from blood vessels and washed repeatedly with 0.15M NaCl, pH 7.4. It was cut to pieces and then macerated with an ultra-turrax, passed through a close-meshed sieve, and extracted four times with four times the volume of acetone. The extraction mixture was filtered by suction to remove the acetone, the residue was dried under vacuum, and then repeatedly extracted with petroleum ether (40–60) using twice the volume of the original brain homogenate. The combined extracts were filtered, dried at 45° C., and dissolved in ether (one fifth of the original brain volume). The mixture was treated with five times the volume of acetone, and the resulting precipitate was collected by suction-filtration, dried and stored under $N_2$ at -20° C. in the dark. Bovine brain phospholipids were weighed into glass tubes and shaken in a vortex mixer (Heidolph) in the presence of five small glass beads ($\phi$ 4 mm) for 1 min. The phospholipids were suspended in 0.15M NaCl, pH 7.4, to a final concentration of 5 mg/ml. The mixture was purged with $N_2$ for 1 min and vigorously dispersed in a vortex mixer for 5 min. The liposomes were allowed to swell for 1 h at 4° C., and vesicles with a mean size of 1–10 $\mu$m were obtained, Bangham, A. D. et al., "Diffusion of Univalent Ions Across the Lamellae of Swollen Phospholipids", *J. Mol. Biol.,* 1965, 13:238–252.

The following reagents were added to glass tubes in the order and at the final concentrations stated. 0.3 ml $KH_2PO_4$-KOH buffer, pH 7.4 (30 mM), 0.29 ml $H_2O$ bidist., 0.2 ml liposomes (1 mg/ml), 0.2 ml $FeCl_3 \cdot 6 H_2O$ (0.1 mM), 0.01 ml anthracenone derivative (variable concentrations). Appropriate blanks and controls with the vehicles (acetone) were conducted. The final reaction volumes were standardized to 1.0 ml. The reaction mixtures were incubated for 1 h at 37° C. in a shaking water bath. 10 L of 20% (w/v) BHT, 0.5 ml 25% (w/v) HCl and 0.5 ml of 1% 2-thiobarbituric acid were added and the samples were heated at 100° C. for 15 min and then cooled in an ice bath (5 min). 2.0 ml of 1-butanol were added and the mixtures were vigorously shaken in a vortex mixer (Heidolph) for 15 s. The organic layer was separated by centrifugation at 3000 rpm (15 min) and the absorbance at 532 nm was measured against butanol.

The results of these determinations for compounds Ia–Iu and IIa–IIr are given in Tables I and II.

EXAMPLE 5
Bovine PMNL 5-Lipoxygenase Assay

Polymorphonuclear leukocytes (PMNL) were prepared from sodium EDTA-anticoagulated bovine blood, essentially as described by Walstra, P. et al., "Leukotriene Formation by Bovine Polymorphonuclear Leukocytes", *Biochim. Biophys. Acta,* 795, 499–503 (1984). Contaminating platelets were removed by repeated centrifugations at 100 g for 20 min. The purified PMN leukocytes were suspended at a concentration of $1 \times 10^7$ cells/ml in phosphate buffered saline (PBS, composed of 8.00 g NaCl, 0.20 g KCl, 1.00 g $Na_2HPO_4 \cdot 2H_2O$, 0.15 g $NaH_2PO_4 \cdot H_2O$, 0.20 g $KH_2PO_4$, adjusted to pH 7.4 with 3N $NH_3$ in a final volume of 1000 ml bidist. $H_2O$). Cell counts were conducted with a Sysmex microcellcounter CC-130. Preincubation was performed with 2.4 ml of the suspension and 10 $\mu$l of a DMSO stock solution of test compounds at the desired concentrations in PBS or vehicle control (DMSO at final concentration of 0.4%) for 15 min at 37° C. in a shaking water bath. The syntheses of $LTB_4$ and 5-HETE were stimulated by the addition of $CaCl_2$ and Ca-ionophore A23187 (final concentrations 2 mM and 20 $\mu$M, respectively), and the incubation was conducted for 10 min at 37° C. 5-LO product formation was terminated by the addition of 3.0 ml of methanol/acetonitrile (1+1) containing NDGA as radical scavenger (final concentration 0.01 mM) and prostaglandin $B_2$ as chromatographic marker (final concentration 0.3 $\mu$M). The incubation mixture was kept in an ice bath for 20 min and then centrifuged at 4000 g for 5 min at 0° C. The supernatant was diluted with 5 ml of water and passed through a prewashed (10 ml of methanol and 5 ml of water, sequentially) octadecylsilane reversed phase cartridge (Baker). The eicosanoids were eluted with 3 ml of methanol, diluted with 3 ml of water and subjected to reversed phase HPLC analysis. This was performed on a 250×4 mm column packed with Nucleosil $C_{18}$ (7 $\mu$m particles; Bischoff, Leonberg, Germany). The isocratic elution conditions of $LTB_4$ were THF/methanol/water/acetic acid (25+30+45+0.1), adjusted to pH 5.5 with conc. $NH_3$, at a flow rate of 0.9 ml/min (Kontron 420 pump), monitored at 280 nm with a Kontron 735 LC UV detector, whereas 5-HETE was monitored at 232 nm using methanol/water/acetic acid (77+23+0.1), pH 5.5, flow rate 1.0 ml/min. Data were recorded on a MacLab data acquisition system (WissTech, Germany) and analysis was performed with the application Peaks on an Apple Macintosh Quadra 700 computer. Integrated areas of the peaks were compared to the $PGB_2$ internal standard and to external standards of authentic samples. Molar absorption coefficients of Samuelsson et al., Borgeat, P. and B. Samuelsson, "Arachidonic Acid Metabolism in Polymorphonuclear Leukocytes: Effects of Ionophore A23187", *Proc. Nat. Acad. Sci. USA*, 76, 2148–2152 (1979), were used for calculations. Inhibition was calculated by the comparison of the mean values of test compound (n=3) with control (n=6–8) activity: (1-test compound/control) ×100. Inhibition was statistically significant compared to that of the control (Student's t-test: $p<0.05$). Each $IC_{50}$ value was derived by interpolation of a log dose vs response plot using four or more concentrations of the compound, spanning the 50% inhibition point.

By the above method, the anthracenone derivatives of the invention were evaluated for their ability to inhibit the production of $LTB_4$ and 5-HETE in isolated bovine polymorphonuclear leucocytes (PMNL), see Walstra, P. et al., "Leukotriene Formation by Bovine Polymorphonuclear Leukocytes", *Biochim. Biophys. Acta*, 795, 499–503 (1984); Dannhardt, G. and also M. Lehr, "In-Vitro Evaluation of 5-Lipoxygenase and Cyc10-Oxygenase Inhibitors Using Bovine Neutrophils and Platelets and HPLC", *J. Pharm. Pharmacol.*, 44, 419–424 (1992). $LTB_4$ and 5-HETE concentrations were measured by reversed-phase HPLC with UV detection. Table I summarizes the inhibitory potencies of the new compounds as expressed by their $IC_{50}$ values. The effect of anthralin itself on arachidonic acid lipoxygenation was previously reported. In human neutrophils and in bovine neutrophils it inhibits the production of $LTB_4$ with an $IC_{50}$ value of 7–74 $\mu M$ (depending on cell density) and 37 $\mu M$, respectively, Schroder, J. -M., "Anthralin (1,8-Dihydroxyanthrone) is a Potent Inhibitor of Leukotriene Production and $LTB_4$-ω Oxidation by Human Neutrophils", *J. Invest. Dermatol.*, 87, 624–629 (1986); Tanzer, H. et al., "Anthralin Derivatives—Inhibition of 5-Lipoxygenase—Antipsoriatic Efficacy", *Arch. Pharm. (Weinheim)*, 324, 841–846 (1991). Several compounds of the invention had $IC_{50}$ values ranging between 0.3 and 0.6 $\mu M$ and were far more potent than anthralin (37 $\mu M$ in this test). For comparison, triacetoxyanthracene and butantrone, which had been in clinical trials for the treatment of psoriasis, are only moderate inhibitors with values of 15% inhibition at 30 $\mu M$ and 38% inhibition at 30 $\mu M$, respectively, in this test.

The 10-phenylacyl-substituted derivatives showed consistently high activity. In the 10-phenylalkylidene series, the phenolic analogues IIp–IIr significantly inhibited $LTB_4$ formation. Only these compounds show keto-enol tautomerism and their deprotonated forms are resonance-stabilized anions. This is important since the anthralin anion is the key intermediate in the oxidation process, which involves a one-electron transfer from the anion to oxygen to give anthralin-10-yl free radical and active oxygen species, Muller et al., "Formation of Active Oxygen Species by Dithranol, III. Dithranol, Active Oxygen Species and Lipid Peroxidation in Vivo", *Arch. Pharm. (Weinheim)*, 320, 59–66 (1987).

The results of this procedure (for compounds Ia–Iu and IIa–IIr) are given in Tables I and II.

EXAMPLE 6

Methods of Synthesis

There are hereafter provided processes by which the 10-substituted anthracenone compounds described in Table I and in Table II were produced. Such procedures, and procedures adapted therefrom, will allow one skilled in the art to prepare numerous of similar compounds.

According to an embodiment of the invention, a 10-phenylacyl functionality was introduced onto an anthracenone nucleus (compounds Ia–Iu in Table I) by reaction of appropriate acyl chlorides with anthralin under weakly basic conditions such that acylation takes place at the C-10 position via the carbanion. See Van Duuren, B. L., et al., "I. Structure and Tumor-Promoting Activity of Analogues of Anthralin (1,8-Dihydroxy-9-Anthrone), *J. Med. Chem.*, 21, 26–31 (1978).

Acyl chlorides were prepared from the corresponding acids according to literature methods, Kratzl, K. et al., "IV. Mitteilung: Zur Chemie des Vanillins und Seiner Derivate", *Monatsh. Chem.*, 83, 1045–1054 (1952); Clark, C. R. and T. W. Davenport, "Anticonvulsant Activity of Some 4-Aminophenylacetamides", *J. Pharm. Sci.*, 76, 18–20 (1987). Because ether cleavage of Ic with boron tribromide resulted in loss of the acyl function at C-10, the desired phenolic analogues Ir–Iu were prepared via hydrogenolytic cleavage of the benzyl ethers Id–If and Il.

The above-described processes for forming compounds Ia–Iu in Table I are illustrated in FIG. 1 wherein R and X are defined in Table I; typical reaction conditions and reagents were as follows: for step (a) pyridine, toluene, 80° C.; and typical reaction conditions and reagents for step (b) were IIa–IIr as follows: Pd-C, $H_2$, THF, room temperature, atmospheric pressure.

Figure 2:
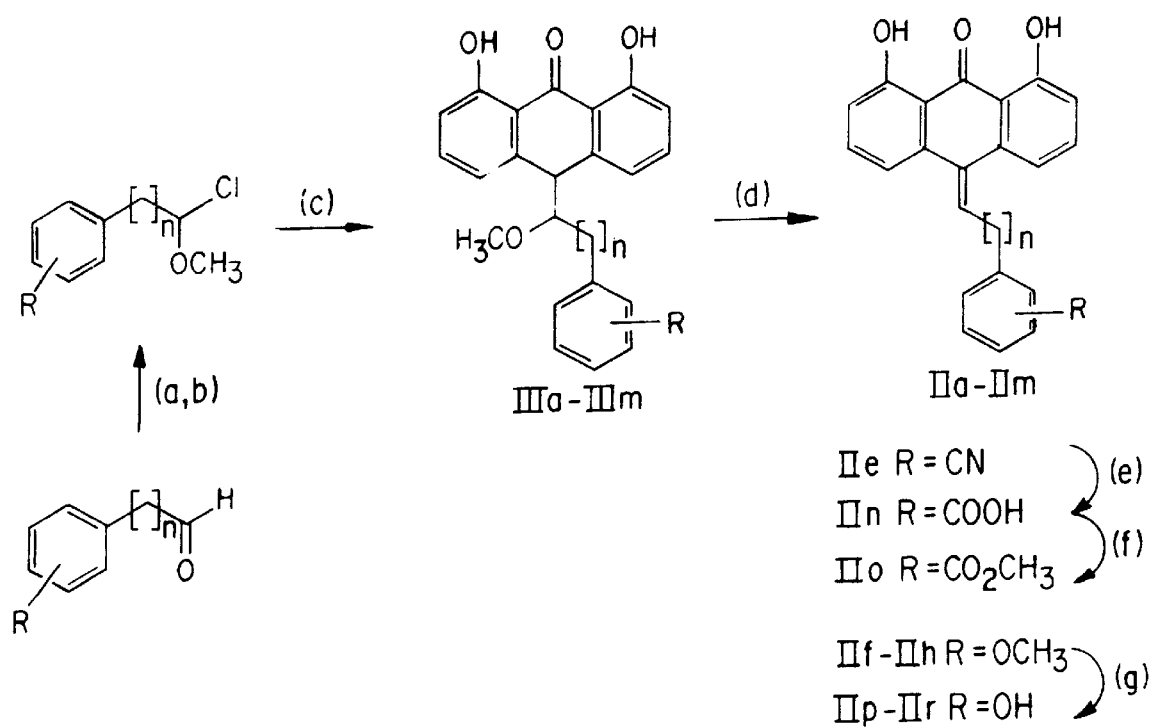
FIG. 2 depicts a representative reaction scheme is suitable for the production of 10-phenylalkylidene 9-anthracenone compounds of the invention.

Another embodiment of the invention for preparation of phenylalkylidene derivatives IIa–IIr is illustrated in FIG. 2. A new method for attaching carbon substituents to the 10-position of anthralin was devised that is based on α-chloro methyl ethers. α-chloro methyl ethers as appropriate were provided by converting suitable aldehydes to their dimethyl acetals, followed by treatment with acetyl chloride. In most cases, the α-chloro methyl ethers were used in crude form because purification led to decomposition. Alkylation of anthralin with α-chloro methyl ethers in the presence of the non-nucleophilic base 1,8-diazabicyclo-[5.4.0]-undec-7-ene (DBU) at 0° C. gave the 1,8-dihydroxy-10-(arylmethoxymethyl)-9(10H)-anthracenones IIIa–IIIm. Base catalyzed (pyridine) elimination of a molecule of methanol afforded IIa–IIh and IIj–IIm in good yields. Derivative IIo was obtained by acid hydrolysis of the benzonitrile IIe and subsequent esterification of the acid IIn. The 10-hydroxyphenylmethylene derivatives IIp–IIr were obtained by deprotection of the corresponding methyl ethers IIf–IIh with boron tribromide in methylene chloride. IIi was prepared selectively from IIIi by reaction with DBU (3 min) which resulted in a 1,2-elimination of methanol.

The above-described processes for forming the compounds IIa–IIr disclosed in Table II are illustrated in FIG. 2 wherein R and n are defined in Table II, typical reagents for step (a) are: trimethyl orthoformate, MeOH, conc. $H_2SO_4$; typical reagents and conditions for step (b) are as follows: acetyl chloride, $SOCl_2$, 80° C.; typical reagents and conditions for step (c) are as follows: anthralin, DBU, $CH_2Cl_2$, $N_2$, 0° C.; typical reagents and conditions for step (d) are as follows: pyridine, $N_2$, 116° C.; typical reagents for step (e) are as follows: $H_2SO_4$ 50%, glacial acetic acid; typical reagents for step (f) are as follows: MeOH, conc. $H_2SO_4$; typical reagents and conditions for step (g) are as follows: $BBr_3$, $CH_2Cl_2$, −70° C.

I. Preparation of Acyl Chlorides

Acyl chlorides were prepared following standard literature procedures, Clark, C. R. and T. W. Davenport, "Anticonvulsant Activity of Some 4-Aminophenylacetamides", *J. Pharm. Sci.*, 76, 18–20 (1987). In most cases the crude products were used in the subsequent acylation steps.

General Procedure for the Preparation of 1,8-Dihydroxy-10-(1-oxo-2-phenylalkyl)-9(10H)-anthracenones Ia–Iq. To a solution of anthralin (1.13 g, 5 mmol) in absolute toluene (80 ml) and dry pyridine (0.55 ml, 7 mmol) was added dropwise a solution of the appropriate acyl chloride (7 mmol) in absolute toluene (10 ml). The reaction mixture was heated to 80° C. for 3 h, cooled, filtered, and the filtrate was evaporated. The residue was purified by chromatography using the indicated eluant (see Table III). The purified fraction was concentrated and a small amount of hexane was added to induce precipitation (see Auterhoff, H. and F. C. Scherff, "Die Dianthrone der Pharmazeutisch Interessierenden Hydroxyanthrachinone", Arch. Pharm. (Weinheim), 293, 918–925 (1960)).

1,8-Dihydroxy-10-(1-oxo-2-phenylethyl)-9(10H)-anthracenone (Ia) was prepared from phenylacetyl chloride as described above. Recrystallization from toluene gave yellow crystals (0.62 g, 36%); mp 178–179° C.; $^1$H-NMR (CDCl$_3$) δ 12.30 (s, 2H), 7.60-6.65 (m, 11H), 5.28 (s, 1H), 3.30 (s, 2H); FTIR 1720 (CO), 1640 cm$^{-1}$ (CO ... HO); UV (CH$_2$Cl$_2$) λ$_{max}$ (log ε) 360 (4.09), 283 (4.05), 261 nm (4.06); MS m/z 344 (4%). Anal. (C$_{22}$H$_{16}$O$_4$) C, H.

1,8-Dihydroxy-10-[2-(4-nitrophenyl)-1-oxoethyl]-9(10H)-anthracenone (Ib) was prepared from 4-nitrophenylacetyl chloride, see, for example, Clark, C. R. and T. W. Davenport, "Anticonvulsant Activity of Some 4-Aminophenylacetamides", J. Pharm. Sci., 76, 18–20 (1987), and as described above, but the reaction mixture was stirred at room temperature. Ib was obtained as yellow crystals (0.29 g, 15%): mp 209–211° C.; $^1$H-NMR (DMSO-d$_6$) δ 12.00 (s, 2H), 8.25-6.95 (m, 10H), 5.70 (s, 1H), 4.00 (s, 2H); FTIR 1713 (CO), 1632 (CO ... OH), 1515 cm$^{-1}$ (NO$_2$); UV (CHCl$_3$) λ$_{max}$ (log ε) 361 (4.08), 271 nm (4.35); MS m/z 389 (5%). Anal. (C$_{22}$H$_{15}$NO$_6$) C, H, N.

1,8-Dihydroxy-10-[2-(4-methoxyphenyl)-1-oxoethyl]-9(10H)-anthracenone (Ic) was prepared from 4-methoxyphenylacetyl chloride, see, for example, Suryawanshi, S. N. and P. F. Fuchs, "Use of an Axial α-Face Control Element in Intramolecular Conjugate Additions: Synthesis of an ABCD Tetracyclic Bruceantin Precursor", J. Org. Chem., 51, 902–921 (1986), and as described above. Recrystallization from toluene gave yellow crystals (0.84 g, 45%); mp 169–170° C.; $^1$H-NMR (CDCl$_3$) δ 12.25 (s, 2H), 7.60-6.65 (m, 10H), 5.25 (s, 1H), 3.70 (s, 3H), 3.25 (s, 2H); FTIR 1708 (CO), 1632 cm$^{-1}$ (CO ... OH), 1515 cm$^{-1}$ (NO$_2$); UV (CH$_2$Cl$_2$) λ$_{max}$ (log ε) 360 (4.09), 283 (4.19), 263 (4.21), 228 nm (4.35); MS m/z 374 (3%). Anal. (C$_{23}$H$_{18}$O$_5$) C, H.

1,8-Dihydroxy-10-[1-oxo-2-(4-phenylmethoxyphenyl) ethyl]-9(10H)-anthracenone (Id) was prepared from 4-(phenylmethoxy)phenylacetyl chloride, see Kratzl, K. and G. Billek, "Die Synthese des d,I-Coclaurins. IV. Mitteilung: Zur Chemie des Vanillins und Seiner Derivate", Monatsh. Chem., 83, 1045–1054 (1952), and as described above, but the reaction mixture was stirred at room temperature. Recrystallization from toluene gave yellow needles (0.90 g, 40%); mp 162–163° C.; $^1$H-NMR (CDCl$_3$) δ 2.25 (s, 2H), 7.55-6.55 (m, 15H), 5.28 (s, 1H), 4.98 (s, 2H), 3.30 (s, 2H); FTIR 1720 (CO), 1630 (CO ... OH); UV (CHCl$_3$) λ$_{max}$ (log ε) 359 (4.08), 283 (4.06), 260 nm (4.13); MS m/z 450 (1%). Anal. (C$_{29}$H$_{22}$O$_5$) C, H.

1,8-Dihydroxy-10-{1-oxo-2-[3,4-bis(phenylmethoxy) phenyl]ethyl}-9(10H)-anthracenone (Ie) was prepared from 3,4-bis(phenylmethoxy)phenylacetyl chloride, see Carlsson, A. et al., "Synthese von Catechol-O-Methyl-Transferase-Hemmenden Verbindungen, in den Catecholaminmetabolismus Eingreifende Substanzen", Helv. Chim. Acta, 45, 270–276 (1962), and as described above, but the reaction mixture was stirred at room temperature. Recrystallization from toluene gave light yellow needles (0.42 g, 30%); mp 147–149° C.; $^1$H-NMR (CDCl$_3$) δ 12.20 (s, 2H), 7.45-6.15 (m, 19H), 5.20 (s, 1H), 5.02 (s, 2H), 4.90 (s, 2H), 3.25 (s, 2H); FTIR 1721 (CO), 1630 cm$^{-1}$ (CO ... OH); UV (CHCl$_3$) λ$_{max}$ (log ε) 360 (4.04), 282 (4.08), 262 (4.12) nm; MS (PI-FD) m/z 556.6 (100%). Anal. (C$_{36}$H$_{28}$O$_6$) C, H.

1,8-Dihydroxy-10-{1-oxo-2-[3,4,5-tris (phenylmethoxyphenyl)]ethyl}-9(10H)-anthracenone (If) was prepared from 3,4,5-tris(phenylmethoxy)phenylacetyl chloride, which was obtained from the appropriate acid, see Carlsson, A. et al., "Synthese von Catechol-O-Methyl-Transferase-Hemmenden Verbindungen, in den Catecholaminmetabolismus Eingreifende Substanzen", Helv. Chim. Acta, 45, 270–276 (1962), and as described above, but the reaction mixture was stirred at room temperature. Recrystallization from toluene/hexane gave yellow needles (0.50 g, 15%); mp 124–125° C.; $^1$H-NMR (CDCl$_3$) δ 12.25 (s, 2H), 7.50-6.70 (m, 21H), 6.00 (s, 2H), 5.22 (s, 1H), 4.95 (s, 2H), 4.90 (s, 4H), 3.22 (s, 2H); FTIR 1725 (CO), 1632 cm$^{-1}$ (CO ... OH); UV (CHCl$_3$) λ$_{max}$ (log ε) 360 (4.02), 239 nm (4.32); MS m/z 662 (56). Anal. (C$_{43}$H$_{34}$O$_7$) C, H.

1,8-Dihydroxy-10-{2-(3,5-bis(1,1-dimethylethyl)-4-hydroxyphenyl]-1-oxo-ethyl}-9(10H)-anthracenone (Ig) was prepared from 4-hydroxy-3,5-bis(1,1-dimethylethyl) phenylacetyl chloride, which was obtained from the appropriate acid, see Ershov, V. V. and I. S. Beolstotskaya, "Synthesis of Hydroxyphenylacetic Acids in the Series of Sterically Hindered Phenols", Bull. Acad. Sci. USSR, Div. Chem. Sci. (Engl. Transl.), 2, 358–360 (1965), and as described above, but the reaction mixture was stirred at room temperature for 3 h. Recrystallization from toluene/hexane and gave yellow crystals (0.80 g, 34%); mp 184–186° C.; $^1$H-NMR (CDCl$_3$) δ 12.20 (s, 2H), 7.55-6.70 (m, 6H), 6.45 (s, 2H), 5.25 (s, 1H), 5.02 (s, 1H), 3.30 (s, 2H), 1.20 (s, 18H); FTIR 3558 (OH), 1704 (CO), 1634 cm$^{-1}$ (CO ... OH); UV (CHCl$_3$) λ$_{max}$ (log ε) 3591 (4.05), 283 (4.03), 261 nm (4.12); MS m/z 472 (7%). Anal. (C$_{30}$H$_{32}$O$_5$) C, H.

1,8-Dihydroxy-10-(1-oxo-3-phenylpropyl)-9(10H)-anthracenone (Ih) was prepared from 3-phenylpropionyl chloride as described above, and gave yellow crystals (0.70 g, 40%); mp 126–128° C.; $^1$H-NMR (CDCl$_3$) δ 12.35 (s, 2H), 7.60-6.80 (m, 11H), 5.25 (s, 1H), 2.75-2.20 (m, 4H); 1707 (CO), 1630 cm$^{-1}$ (CO ... OH); UV (CHCl$_3$) λ$_{max}$ (log ε) 359 (4.06), 281 (4.03), 261 nm (4.03); MS m/z 358 (5%). Anal. (C$_{23}$H$_{18}$O$_4$) C, H.

1,8-Dihydroxy-10-(3-(4-methoxyphenyl)-1-oxopropyl)-9(10H)-anthracenone (Ii) was prepared from 3-(4-methoxyphenyl)propionyl chloride, see G. Barger and G. S. Walpole, "Further Synthesis of p-Hydroxyphenylethylamine", J. Chem. Soc., 95, 1720–1724 (1909), and as described above, and gave a yellow powder (0.33 g, 17%); mp 108–110° C.; $^1$H-NMR (CDCl$_3$) δ 12.50 (s, 2H), 7.70-6.80 (m, 10H), 5.20 (s, 1H), 3.9 (s, 3H), 2.90-2.70 (t, 2H), 2.60-2.40 (t, 2H); 1711 (CO), 1632 cm$^{-1}$ (CO ... OH); UV (MeOH) λ$_{max}$ (log ε) 358 (3.94), 297 nm (4.23); MS m/z 388 (2.3%). Anal. (C$_{24}$H$_{20}$O$_5$) C, H.

1,8-Dihydroxy-10-[3-(3,4-dimethoxyphenyl)-1-oxopropyl]-9(10H)-anthracenone (Ij) was prepared from 3-(3,4-dimethoxyphenyl)propionyl chloride, see Carroll, R. and P. E. Spoerri, "The Synthesis of 1,4-di-(3',4'-Dimethoxyphenyl)-Butanone (Veratrylhomoveratrylketone)", J. Am. Chem. Soc., 60, 2656–2658 (1938), and as described above, and gave a yellow powder (0.21 g, 10%); mp 115–118° C.; $^1$H-NMR (CDCl$_3$) δ 12.30 (s, 2H), 7.60-6.30 (m, 9H), 5.20 (s, 1H), 3.9 (s, 3H), 3.85 (s, 3H), 2.70-2.50 (t, 2H), 2.40–2.20 (t, 2H); 1711 (CO), 1630 cm$^{-1}$ (CO . . . OH); UV (MeOH) λ$_{max}$ (log ε) 360 (4.01), 281 nm (4.09); MS m/z 418 (1.2%). Anal. (C$_{25}$H$_{22}$O$_6$) C, H.

1,8-Dihydroxy-10-[3-(3,4,5-trimethoxyphenyl)-1-oxopropyl]-9(10H)-anthracenone (Ik) was prepared from 3-(3,4,5-trimethoxyphenyl)propionyl chloride, see Michalsky, J. and L. Sadilek, "Uber die Roten Anile", *Mitt. Monatsh. Chem.*, 90, 171–178 (1959), and as described above, and gave a yellow powder (0.92 g, 41%); mp 118–120° C.; $^1$H-NMR (CDCl$_3$) δ 12.40 (s, 2H), 7.60-6.10 (m, 8H), 5.20 (s, 1H), 3.9 (s, 3H), 3.80 (s, 6H), 2.75–2.50 (t, 2H), 2.40-2.20 (t, 2H); 1719 (CO), 1634 cm$^{-1}$ (CO . . . OH); UV (MeOH) λ$_{max}$ (log ε) 360 (4.06), 281 (4.08), 262 nm (4.12); MS m/z 448 (2.6%). Anal. (C$_{26}$H$_{24}$O$_7$) C, H.

1,8-Dihydroxy-10-[1-oxo-3-(4-phenylmethoxyphenyl)propyl]-9(10H)-anthracenone (Il) was prepared from 3-[4-(phenylmethoxy)phenyl]propionyl chloride, see Doherty, D. G., "The Hydrolysis of Carbon—Carbon Bonds by α-Chrymotrypsin", *J. Am. Chem. Soc.*, 77, 4887–4892 (1955), and as described above, although the reaction mixture was stirred at 50° C., and gave a yellow powder (0.84 g, 36%); mp 140–142° C.; $^1$H-NMR (CDCl$_3$) δ 12.30 (s, 2H), 7.50-6.70 (m, 15H), 5.20 (s, lH), 5.00 (s, 2H), 2.70-2.20 (m, 4H); 1710 (CO), 1630 cm$^{-1}$ (CO . . . OH); UV (MeOH) λ$_{max}$ (log ε) 359 (4.05), 282 (4.06), 268 nm (4.07); MS m/z 464 (2.7%). Anal. (C$_{23}$H$_{24}$O$_5$) C, H.

(E)-1,8-Dihydroxy-10-(1-oxo-3-phenyl-2-propenyl)-9(10H)-anthracenone (Im) was prepared from trans-cinnamoyl chloride as described above, but the reaction mixture was stirred at room temperature, and gave yellow crystals (0.53 g, 30%); mp 205–208° C.; $^1$H-NMR (CDCl$_3$) δ 12.40 (s, 2H), 8.80-6.90 (m, 11H), 7.58 (d, 1H, J=16.5 Hz), 6.28 (d, 1H, J=?), 5.40 (s, 1H); 1684 (CO), 1634 cm$^{-1}$ (CO . . . OH); UV (MeOH) λ$_{max}$ (log ε) 358 (4.10), 297 nm (4.40); MS m/z 356 (0.7%). Anal. (C$_{23}$H$_6$O$_4$) C, H.

(E)-1, 8-Dihydroxy-10-[3-(4-nitrophenyl)-1-oxo-2-propenyl]-9(10H)-anthracenone (In) was prepared from trans-4-nitrocinnamoyl chloride, see Anschutz, R., "Uber die Zersetzung von Fumarsaure—Und Zimtsaure-Arylester Durch Hitze Zu Symm. Diaryl-Athylenen", *Ber. Dtsch. Chem. Ges.*, 60, 1320–1322 (1927), and as described above, but the reaction mixture was stirred at room temperature, and gave yellow crystals (0.10 g, 5%); mp 225° C. (decomposition); $^1$H-NMR (CDCl$_3$) δ 12.40 (s, 2H), 8.20-6.80 (m, 11H), 6.40-6.20 (d, 1H), 5.40 (s, 1H); 1667 (CO), 1609 cm$^{-1}$ (CO . . . OH); UV (CHCl$_3$) λ$_{max}$ (log ε) 316 (4.41), 292 nm (4.38); MS m/z 401 (4.0%). Anal. (C$_{23}$H$_{15}$NO$_6$) C, H, N.

(E)-1,8-Dihydroxy-10-[3-(3-methoxyphenyl)-1-oxo-2-propenyl]-9(10H)-anthracenone (Io) was prepared from trans-3-methoxycinnamoyl chloride, Borsche, W. and C. K. Bodenstein, "Untersuchungen Uber Die Bestandteile Der Kawawurzel, IX: Die Synthese des Yangonins", *Ber. Dtsch. Chem. Ges.*, 62, 2515–2523 (1929), and as described above, but the reaction mixture was stirred at room temperature, and gave yellow needles (0.70 g, 36%); mp 162–166° C.; $^1$H-NMR (CDCl$_3$) δ 12.40 (s, 2H), 7.70-6.80 (m, 11H), 6.40-6.10 (d, 1H), 5.30 (s, 1H), 3.8 (s, 3H); 1679 (CO), 1629 cm$^{-1}$ (CO . . . OH); UV (MeOH) λ$_{max}$ (log ε) 348 (4.21), 293 nm (4.36); MS m/z 386 (3.5%). Anal. (C$_{24}$H$_{18}$O$_4$) C, H.

1,8-Dihydroxy-10-(1-oxo-4-phenylbutyl)-9(10H)-anthracenone (Ip) was prepared from phenylbutyryl chloride, see Kipping, F. S. and A. Hill, "α-ketotetrahydronaphthalene", *J. Chem. Soc.*, 75, 144–153 (1899), and as described above. Recrystallization from toluene/hexane gave yellow needles (0.81 g, 44%); mp 146–147° C.; $^1$H-NMR (CDCl$_3$) δ 12.25 (s, 2H), 7.65-6.85 (m, 11H), 5.25 (s, 1H), 2.40-1.95 (m, 4H), 1.80-1.55 (m, 2H); FTIR 1713 (CO), 1632 cm$^{-1}$ (CO . . . OH); UV (CHCl$_3$) λ$_{max}$ (log ε) 359 (4.08), 281 (4.07), 237 nm (3.96); MS m/z 372 (2%). Anal. (C$_{24}$H$_{20}$O$_4$) C, H.

1,8-Dihydroxy-10-(1-oxo-5-phenylpentyl)-9(10H)-anthracenone (Iq) was prepared from phenylvaleryl chloride, see Fieser, L. F. and L. Teffler, "Naphthoquinone Antimalarials", *J. Am. Chem. Soc.*, 70, 3174–3215 (1948), and gave yellow needles (1.69 g, 43%); mp 128–129° C.; $^1$H-NMR (CDCl$_3$) δ 12.30 (s, 2H), 7.60-6.75 (m, 11H), 5.20 (s, 1H), 2.50-2.20 (m, 2H), 2.15–1.90 (m, 2H), 1.50-1.15 (m, 4H); FTIR 1713 (CO), 1630 cm$^{-1}$ (CO . . . OH); UV (MeOH) λ$_{max}$ (log ε) 359 (4.02), 262 nm (4.11). Anal. (C$_{25}$H$_{22}$O$_4$) C, H.

1,8-Dihydroxy-10-[2-(4-hydroxyphenyl)-1-oxoethyl]-9(10H)-anthracenone (Ir). A solution of Id (0.5 g, 1.11 mmol) in absolute THF (50 ml) was hydrogenated over 10% Pd-C (150 mg) at room temperature and atmospheric pressure. After the requisite amount of hydrogen had been taken up (24 h, TLC-control), the catalyst was removed by filtration and the solution was evaporated. The product was purified by chromatography using CH$_2$Cl$_2$/ether (3+2). The purified fraction was concentrated and a small amount of hexane was added to induce precipitation. Recrystallization from ethanol 99% afforded yellow needles (0.27 g, 70%); mp 178–179° C.; $^1$H-NMR (CDCl$_3$) δ 12.33 (s, 2H), 7.60-6.80 (m, 6H), 6.60 (s, 4H), 5.28 (s, 1H), 4.90 (s, 1H), 3.30 (s, 2H); FTIR 3410 (OH), 1725 (CO), 1705 (CO), 1630 cm$^{-1}$ (CO . . . OH); UV (MeOH) λ$_{max}$ (log ε) 360 (4.04), 261 nm (4.19); MS m/z 360 (7%). Anal. (C$_{22}$H$_6$O$_5$) C, H.

1,8-Dihydroxy-10-[2-(3,4-dihydroxyphenyl)-1-oxoethyl]-9(10H)-anthracenone (Is). For this procedure, compound Ie (0.5 g, 0.90 mmol) was hydrogenated in a manner analogous to that described for Ir to provide yellow needles (0.19 g, 55%); mp 180° C. (decomposition); $^1$H-NMR (DMSO-d$_6$) δ 11.91 (s, 2H), 8.83 (s, 2H), 7.62–6.30 (m, 9H), 5.71 (s, 1H), 3.79 (s, 2H); FTIR 3307 (OH), 1721 (CO), 1632 cm$^{-1}$ (CO . . . OH); UV (MeOH) λ$_{max}$ (log ε) 357 (4.01), 282 (4.05), 262 nm (4.10); MS m/z 376 (0.8%). Anal. (C$_{22}$H$_{16}$O$_6$) C, H.

1,8-Dihydroxy-10-[2-(3,4,5-trihydroxyphenyl)-1-oxoethyl]-9(10H)-anthracenone (It). For this procedure, compound If (0.5 g, 0.75 mmol) was hydrogenated in a manner analogous to that described for Ir to provide yellow crystals (0.24 g, 80%); mp 200° C. (decomposition); $^1$H-NMR (DMSO-d$_6$) δ 11.89 (s, 2H), 8.77 (s, 3H), 7.61-6.93 (m, 6H), 6.00 (s, 2H), 5.70 (s, 1H), 3.73 (s, 2H); FTIR 3432 (OH), 1696 (CO), 1634 cm$^{-1}$ (CO . . . OH); UV (CHCl$_3$) λ$_{max}$ (log ε) 359 (3.97), 261 nm (4.06); MS m/z 392 (5%). Anal. (C$_{22}$H$_{16}$O$_7$) C, H.

1,8-Dihydroxy-10-[3-(4-hydroxyphenyl)-1-oxopropyl]-9(10H)-anthracenone (Iu). For this procedure, compound Il (0.24 g, 0.50 mmol) was hydrogenated in a manner analogous to that described for Ir to provide a yellow powder (0.11 g, 45%); mp 190–194° C.; $^1$H-NMR (CDCl$_3$) δ 12.30 (s, 2H), 7.60-6.50 (m, 10H), 5.20 (s, 1H), 4.6 (s, 1H), 2.70-2.20 (m, 4H); 3352 (OH), 1688 (CO), 1632 cm$^{-1}$ (CO . . . OH); UV (MeOH) λ$_{max}$ (log ε) 359 (4.03), 282 (4.07), 268 nm (4.07); MS m/z 374 (10.7%). Anal. (C$_{23}$H$_{18}$O$_5$) C, H.

II. Preparation of α-Chloro Methyl Ethers

Appropriate aldehydes were converted to the corresponding A-dimethyl acetals and then to the α-chloro methyl ethers according to published procedures, J. Klein, and E. D. Bergmann, "The Reaction of Acetals with Malonic Acid and Its Derivatives. A Contribution to the Knowledge of the Knoevennagel-Doebner Reaction", *J. Am. Chem. Soc.*, 79, 3452–3454 (1957); Weidner, R. and E. U. Wurthwein, "2-Azaallenium-Salze aus N-Benzyliden-α-Methoxybenzylaminen, *Chem. Ber.*, 122, 1095–1106 (1989).

General Procedure for the Preparation of 1,8-Dihydroxy-10-[(aryl)methoxymethyl]-9(10H)-anthracenone (IIIa–IIIm). To a solution of anthralin (1 g, 4.4 mmol) and DBU (0.7 g, 4.6 mmol) in dry $CH_2Cl_2$ (50 ml) was added dropwise at 0° C. a solution of the appropriate α-chloro methyl ether (5.5 mmol) in dry $CH_2Cl_2$ (10 ml), and the solution was stirred at 0° C. for 30 min under $N_2$. The reaction mixture was shaken thoroughly with 2N HCl, and then the organic phase was washed with saturated aqueous NaCl, dried over $Na_2SO_4$, and evaporated. The residue was purified by chromatography using $CH_2Cl_2$ or a mixture of $CH_2Cl_2$/hexane, and the concentrated crude product was treated with a small amount of hexane to induce precipitation of the product.

1,8-Dihydroxy-10-[(methoxy)phenylmethyl)]-9(10H)-anthracenone (IIIa) was prepared from (chloromethoxymethyl)benzene, see Weidner, R. and E. U. Wurthwein, "2-Azaallenium-Salze aus N-Benzyliden-α-Methoxybenzylaminen, *Chem. Ber.*, 122, 1095–1106 (1989), as described above. Recrystallization from ethanol/toluene gave yellow crystals (0.60 g, 40%); mp 162–163° C.; $^1$H-NMR (CDCl$_3$) δ 11.90 (s, 1H), 11.80 (s, 1H), 7.55-6.30 (m, 11H), 4.60-4.35 (m, 2H), 3.20 (s, 3H); FTIR 1634 cm$^{-1}$ (CO . . . OH); MS (PI-FD) m/z 346 (20%). Anal. ($C_{22}H_{18}O_4$) C, H.

1,8-Dihydroxy-10-[methoxy(4-methylphenyl)methyl]-9(10H)-anthracenone (IIIb) was prepared from 1-(chloromethoxymethyl)-4-methylbenzene, see Weidner, R. and E. U. Wurthwein, "2-Azaallenium-Salze aus N-Benzyliden-α-Methoxybenzylaminen, Chem. Ber., 122, 1095–1106 (1989), and as described above. Recrystallization from ethanol 99% gave yellow needles (0.52 g, 33%); mp 137–138° C.; $^1$H-NMR (CDCl$_3$) δ 11.85 (s, 1H), 11.75 (s, 1H), 7.50-6.15 (m, 10H), 4.55-4.30 (m, 2H), 3.15 (s, 3H), 2.25 (s, 3H); FTIR 1630 cm$^{-1}$ (CO . . . OH); MS m/z 328 (100%, $M^+$-$CH_3OH$) . Anal. ($C_{23}H_{20}O_4$) C, H.

10-[(4-Trifluoromethylphenyl)methoxymethyl]-1,8-dihydroxy-9(10H)-anthracenone (IIIc) was prepared from 1-(chloromethoxymethyl)-4-trifluoromethylbenzene, which was prepared from 4-(trifluoromethyl)benzaldehyde, and as described above. Recrystallization from ethanol 99% gave yellow needles (0.73 g, 40%); mp 155–156° C.; $^1$H-NMR (CDCl$_3$) δ 11.70 (s, 1H), 11.60 (s, 1H), 7.50-6.30 (m, 10H), 4.45-4.30 (m, 2H), 3.10 (s, 3H); FTIR 1632 cm$^{-1}$ (CO . . . OH); MS m/z 414 (0.03%). Anal. ($C_{23}H_{17}F_3O_4$) C, H.

1,8-Dihydroxy-10-[methoxy(4-nitrophenyl)methyl]-9(10H)-anthracenone (IIId) was prepared from 1-(chloromethoxymethyl)-4-nitrobenzene, see Weidner, R. and E. U. Wurthwein, "2-Azaallenium-Salze aus N-Benzyliden-α-Methoxybenzylaminen, Chem. Ber., 1989, 122:1095–1106, and as described above. Recrystallization from ethanol 99% gave yellow needles (0.69 g, 40%); mp 175–177° C.; $^1$H-NMR (CDCl$_3$) δ 11.80 (s, 1H), 11.70 (s, 1H), 8.00-6.50 (m, 10H), 4.65-4.50 (m, 2H), 3.20 (s, 3H); FTIR 1632 cm$^{-1}$ (CO . . . OH), 1519 cm$^{-1}$ ($NO_2$); MS m/z 391 (0.2%). Anal. ($C_{22}H_{17}NO_6$) C, H, N.

10-[(4-Cyanophenyl)methoxymethyl]-1,8-dihydroxy-9(10H)-anthracenone (IIIe) was prepared from 1-(chloromethoxymethyl)-4-cyanobenzene, which was prepared from 4-cyanobenzaldehyde, as described above. Recrystallization from ethanol/toluene gave yellow needles (0.66 g, 40%); mp 165–166° C.; $^1$H-NMR (CDCl$_3$) δ 11.85 (s, 1H), 11.75 (s, 1H), 7.55-6.40 (m, 10H), 4.60-4.45 (m, 2H), 3.20 (s, 3H); FTIR 2227 (CN), 1630 cm$^{-1}$ (CO . . . OH); MS m/z 371 (0.2%). Anal. ($C_{23}H_{17}NO_4$) C, H.

1,8-Dihydroxy-10-[(4-methoxyphenyl)methoxymethyl]-9(10H)-anthracenone (IIIf) was prepared from 1-(chloromethoxymethyl)-4-methoxybenzene, Weidner, R. and E. U. Wurthwein, "2-Azaallenium-Salze aus N-Benzyliden-α-Methoxybenzylaminen, *Chem. Ber.*, 122, 1095–1106 (1989), and as described above. The product was purified by chromatography and washed with methanol under ultrasonication to give yellow crystals (0.62 g, 37%); mp 133–134° C.; $^1$H-NMR (CDCl$_3$) δ 11.85 (s, 1H), 11.80 (s, 1H), 7.55-6.15 (m, 10H), 4.60-4.35 (m, 2H), 3.70 (s, 3H), 3.15 (s, 3H); FTIR 1634 cm$^{-1}$ (CO . . . OH); MS m/z 344 (0.5%, $M^+$-$CH_3OH$). Anal. ($C_{23}H_{20}O_5$) C, H.

1,8-Dihydroxy-10-[methoxy(3,4-dimethoxyphenyl)methyl]-9(10H)-anthracenone (IIIg) was prepared from 1-(chloromethoxymethyl)-3,4-dimethoxybenzene, which was prepared from 3,4-dimethoxybenzaldehyde, as described above, and gave yellow needles (0.58 g, 32%); mp 144–146° C.; $^1$H-NMR (CDCl$_3$) δ 11.85 (s, 1H), 11.75 (s, 1H), 7.55-5.80 (m, 9H), 4.60-4.30 (m, 2H), 3.80 (s, 3H), 3.50 (s, 3H), 3.20 (s, 3H); FTIR 1632 cm$^{-1}$ (CO . . . OH); MS m/z 406 (0.01%). Anal. ($C_{24}H_{22}O_6$) C, H.

1,8-Dihydroxy-10-[methoxy(3,4,5-trimethoxyphenyl)methyl]-9(10H)-anthracenone (IIIh) was prepared from 1-(chloromethoxymethyl)-3,4,5-trimethoxybenzene, which was prepared from 3,4,5-trimethoxybenzaldehyde, as described above, and gave yellow needles (0.58 g, 34%); mp 130–131° C.; $^1$H-NMR (CDCl$_3$) δ 11.80 (s, 1H), 11.70 (s, 1H), 7.50-6.75 (m, 8H), 4.55-4.30 (m, 2H), 3.70 (s, 3H), 3.45 (s, 6H), 3.25 (s, 3H); FTIR 1632 cm$^{-1}$ (CO . . . OH); MS m/z 436 (0.02%). Anal. ($C_{25}H_{24}O_7$) C, H.

1,8-Dihydroxy-10-(1-methoxy-2-phenylethyl)-9(10H)-anthracenone (IIIi) was prepared from (2-chloro-2-methoxyethyl)benzene, see Lokensgard, J. P. et al., "Synthesis of N-(α-Methoxybenzylaminen", *Chem. Ber.*, 122, 1095–1106 (1989), and as described above, and gave yellow crystals (0.32 g, 20%); mp 140–141° C.; $^1$H-NMR (CDCl$_3$) δ 12.15 (s, 2H), 7.55-6.80 (m, 11H), 4.40 (d, 1H, J=3 Hz), 3.70-3.50 (m, 1H), 3.15 (s, 3H), 2.30-2.10 (m, 2H); FTIR 1632 cm$^{-1}$ (CO . . . OH); MS m/z 360 (0.3%). Anal. ($C_{23}H_{20}O_4$) C, H.

1,8-Dihydroxy-10-(1-methoxy-3-phenylpropyl)-9(10H)-anthracenone (IIIj) was prepared from (3-chloro-3-methoxypropyl)benzene, which was in turn prepared from (3,3-dimethoxypropyl)benzene, see Straus, F. and A. Berkov, "Uber Zimtaldehyd und Phenylvinylketon", *Liebiqs Ann. Chem.*, 401, 121–159 (1913), and as described above, and gave yellow crystals (0.30 g, 18%); mp 138–139° C.; $^1$H-NMR (CDCl$_3$) δ 12.22 (s, 1H), 12.20 (s, 1H), 7.60-6.75 (m, 11H), 4.45 (d, 1H, J=4 Hz), 3.45 (s, 3H), 3.40-3.25 (m, 1H), 2.65–2.25 (m, 2H), 1.40–1.10 (m, 2H); FTIR 1632 cm$^{-1}$ (CO . . . OH); MS m/z 374 (0.2%). Anal. ($C_{24}H_{22}O_4$) C, H.

1,8-Dihydroxy-10-[1-methoxy-3-(4-methoxyphenyl)propyl]-9(10H)-anthracenone (IIIk) was prepared from 1-(3-chloro-3-methoxypropyl)-4-methoxybenzene, which was in turn prepared from 3-(4-methoxyphenyl)propanal, see Semmelhack, M. F. et al., "Reaction of Aryl and Vinyl Halides with Zerovalent Nickel—Preparative Aspects and the Synthesis of Alnusone", *J. Am. Chem. Soc.*, 103, 6460–6471 (1981), and as described above, and gave a yellow powder (0.78 g, 42%); mp 83–85° C.; $^1$H-NMR (CDCl$_3$) δ 12.3 (s, 1H), 12.25 (s, 1H), 7.70-6.60 (m, 10H), 4.50-4.30 (d, 1H, J=?), 3.75 (s, 3H), 3.40 (s, 3H), 3.00-1.00 (m, 5H); FTIR 1630 cm$^{-1}$ (CO . . . OH); MS m/z 404 (2.6%). Anal. (C$_{25}$H$_{24}$O$_5$) C, H.

1,8-Dihydroxy-10-(1-methoxy-4-phenylbutyl)-9(10H)-anthracenone (III1) was prepared from (4-chloro-4-methoxybutyl)benzene, which was prepared from (4,4-dimethoxybutyl)benzene, see von Braun, J. and O. Kruber, "Synthesen in der Fettaromatischen Reihe. III. Amidosauren. Nitroverbindungen. Aldehyde.", *Ber. Dtsch. Chem. Ges.*, 45, 384–402 (1912), and as described above. Chromatography using CH$_2$Cl$_2$/hexane (7+3) gave yellow needles (0.86 g, 25%); mp 128–130° C.; $^1$H-NMR (CDCl$_3$) δ 12.20 (s, 2H), 7.60-6.75 (m, 11H), 4.45 (d, 1H, J=4 Hz), 3.45 (s, 3H), 3.40-3.30 (m, 1H), 2.40 (t, 2H, J=6 Hz), 1.80-0.80 (m, 4H); FTIR 1630 cm$^{-1}$ (CO . . . OH). Anal. (C$_{25}$H$_{24}$O$_4$) C, H.

1,8-Dihydroxy-10-(1-methoxy-5-phenylpentyl)-9(10H)-anthracenone (IIIm) was prepared from (5-chloro-5-methoxypentyl)benzene, which was itself prepared from (5,5-dimethoxypentyl)benzene, see von Braun, J. and O. Kruber, "Synthesen in der Fettaromatischen Reihe. III. Amidosauren. Nitroverbindungen. Aldehyde.", *Ber. Dtsch. Chem. Ges.*, 45, 384–402 (1912), and as described above. Chromatography using CH$_2$Cl$_2$/hexane (7+3) gave yellow crystals (0.61 g, 17%); mp 68° C.; $^1$H-NMR (CDCl$_3$) δ 12.20 (s, 2H), 7.60-6.75 (m, 11H), 4.40 (d, 1H, J=4 Hz), 3.40 (s, 3H), 3.40-3.20 (m, 1H), 2.40 (t, 2H, J=6 Hz), 1.60-1.40 (m, 6H); FTIR 1632 cm$^{-1}$ (CO . . . OH). Anal. (C$_{26}$H$_{26}$O$_4$) C, H.

III. General Procedure for the Preparation of 1,8-Dihydroxy-10-phenylalkyliden-9(10H)-anthracenones IIa–IIh and IIj–IIm A solution of the appropriate 1,8-dihydroxy-10-(arylmethoxymethyl)-9(10H)-anthracenone (IIIa–IIIl, 0.5 g, 1.15–1.44 mmol) in pyridine (10 ml) was refluxed under N$_2$ for 15–30 min, until the reaction was completed (TLC-control). The reaction mixture was then cooled and poured into water (200 ml), acidified with 6N HCl, and extracted with CH$_2$Cl$_2$ (3× 20 ml). The combined CH$_2$Cl$_2$ extracts were washed with saturated aqueous NaCl, dried over Na$_2$SO$_4$, and then evaporated. The residue was purified by chromatography using the indicated eluant (Table III). The concentrated crude product was treated with a small amount of hexane to induce precipitation of the product.

1,8-Dihydroxy-10-(phenylmethylen)-9(10H)-anthracenone (IIa) was prepared from IIIa as described above. Recrystallization from ethanol 99% gave orange-yellow needles (0.41 g, 90%); mp 161° C.; $^1$H-NMR (250 MHz, CDCl$_3$) δ 12.26 (s, 1H), 12.16 (s, 1H), 7.56-6.86 (m, 12H); FTIR 1627 cm$^{-1}$ (CO . . . OH); UV (MeOH) λ$_{max}$ (log ε) 394 (4.06), 234 nm (4.64); MS m/z 314 (44%). Anal. (C$_{21}$H$_{14}$O$_3$) C, H.

1,8-Dihydroxy-10-[(4-methylphenyl)methylen]-9(10H)-anthracenone (IIb) was prepared from IIIb as described above and gave orange-yellow crystals (0.36 g, 80%); mp 146–147° C.; $^1$H-NMR (CDCl$_3$) δ 12.40 (s, 1H), 12.30 (s, 1H), 7.70-6.80 (m, 11H), 2.35 (s, 3H); FTIR 1629 cm$^{-1}$ (CO . . . OH); UV (CH$_2$Cl$_2$) λ$_{max}$ (log ε) 395 (4.07), 317 (4.02), 282 (3.96), 238 nm (4.61); MS m/z 328 (100%). Anal. (C$_{22}$H$_{16}$O$_3$) C, H.

1,8-Dihydroxy-10-[(4-trifluoromethylphenyl)methylene]-9(10H)-anthracenone (IIc) was prepared from IIIc as described above and gave orange-yellow crystals (0.30 g, 65%); mp 151° C.; $^1$H-NMR (CDCl$_3$) δ 12.25 (s, 1H), 12.15 (s, 1H), 7.65-6.80 (m, 11H); FTIR 1630 cm$^{-1}$ (CO . . . OH); UV (CH$_2$Cl$_2$) λ$_{max}$ (log ε) 397 (4.14), 302 (4.15), 236 nm (4.65); MS m/z 382 (100%). Anal. (C$_{22}$H$_{13}$F$_3$O$_3$) C, H.

1,8-Dihydroxy-10-[(4-nitrophenyl)methylen]-9(10H)-anthracenone (IId) was prepared from IIId as described above. Recrystallization from ethanol/toluene gave orange-yellow crystals (0.34 g, 75%); mp 172–175° C.; $^1$H-NMR (CDCl$_3$) δ 12.20 (s, 1H), 12.10 (s, 1H), 8.20-6.75 (m, 11H); FTIR 1630 cm$^{-1}$ (CO . . . OH), 1515 cm$^{-1}$ (NO$_2$); UV (MeOH) λ$_{max}$ (log ε) 400 (4.15), 305 (4.12), 232 nm (4.54); MS m/z 359 (100%). Anal. (C$_{21}$H$_{13}$NO$_5$) C, H, N.

10-[(4-Cyanophenyl)methylene]-1,8-dihydroxy-9(10H)-anthracenone (IIe) was prepared from IIIe as described above, and gave orange-yellow crystals (0.69 g, 76%); mp 209° C.; $^1$H-NMR (CDCl$_3$) δ 12.25 (s, 1H), 12.15 (s, 1H), 7.70-6.80 (m, 11H); FTIR 2225 (CN), 1630 cm$^{-1}$ (CO . . . OH); UV (MeOH) λ$_{max}$ (log ε) 397 (4.12), 304 (4.18), 234 nm (4.63); MS m/z 339 (100%). Anal. (C$_{22}$H$_{13}$NO$_3$) C, H, N.

1,8-Dihydroxy-10-[(4-methoxyphenyl)methylen]-9(10H)-anthracenone (IIf) was prepared from IIIf as described above, and gave orange-yellow needles (0.39 g, 85%); mp 165° C.; $^1$H-NMR (CDCl$_3$) δ 12.30 (s, 1H), 12.20 (s, 1H), 7.60-6.70 (m, 11H), 3.80 (s, 3H); FTIR 1627 cm$^{-1}$ (CO . . . OH); UV (MeOH) λ$_{max}$ (log ε) 444 (3.99), 392 (4.07), 334 (4.00), 284 (4.04), 238 nm (4.63); MS m/z 344 (100%). Anal. (C$_{22}$H$_{16}$O$_4$) C, H.

1,8-Dihydroxy-10-[(3,4-dimethoxyphenyl)methylen]-9(10H)-anthracenone (IIg) was prepared from IIIg as described above, and gave orange-red crystals (0.40 g, 87%); mp 158° C.; $^1$H-NMR (CDCl$_3$) δ 12.30 (s, 1H), 12.20 (s, 1H), 7.55-6.75 (m, 10H), 3.95 (s, 3H), 3.75 (s, 3H); FTIR 1629 cm$^{-1}$ (CO . . . OH); UV (CHCl$_3$) λ$_{max}$ (log ε) 451 (3.75), 396 (3.86), 287 nm (4.01); MS m/z 374 (100%). Anal. (C$_{23}$H$_{18}$O$_5$) C, H.

1,8-Dihydroxy-10-[(3,4,5-trimethoxyphenyl)methylen]-9(10H)-anthracenone (IIh) was prepared from IIIh as described above, and gave orange-red needles (0.39 g, 84%); mp 211–212° C.; $^1$H-NMR (CDCl$_3$) δ 12.30 (s, 1H), 12.15 (s, 1H), 7.65-6.85 (m, 7H), 6.50 (s, 2H), 3.90 (s, 3H), 3.75 (s, 6H); FTIR 1632 cm$^{-1}$ (CO . . . OH); UV (CHCl$_3$) λ$_{max}$ (log ε) 399 (4.07), 332 (3.92), 288 nm (4.08); MS m/z 404 (100%). Anal. (C$_{24}$H$_{20}$O$_6$) C, H.

1,8-Dihydroxy-10-(3-phenylpropyliden)-9(10H)-anthracenone (IIj) was prepared from IIIj as described above, and gave yellow crystals (0.42 g, 52%); mp 143–144° C.; $^1$H-NMR (CDCl$_3$) δ 12.30 (s, 1H), 12.20 (s, 1H), 7.60-6.40 (m, 12H), 2.85 (s, 4H); FTIR 1630 cm$^{-1}$ (CO . . . OH); UV (CH$_2$Cl$_2$) λ$_{max}$ (log ε) 384 (4.12), 296 nm (4.09); MS m/z 342 (25%). Anal. (C$_{23}$H$_{18}$O$_3$) C, H.

1,8-Dihydroxy-10-[3-(4-methoxyphenylpropyliden)-9(10H)-anthracenone (IIk) was prepared from IIIk as described above, and gave an orange-yellow powder (0.22 g, 47%); mp 134–136° C.; $^1$H-NMR (CDCl$_3$) δ 12.40 (s, 1H), 12.30 (s, 1H), 7.60-6.50 (m, 11H), 3.80 (s, 3H), 2.90-2.70 (m, 4H); FTIR 1630 cm$^{-1}$ (CO . . . OH); UV (MeOH) λ$_{max}$ (log ε) 385 (4.09), 286 nm (4.09); MS m/z 372 (9.2%). Anal. (C$_{24}$H$_{20}$O$_4$) C, H.

1,8-Dihydroxy-10-[4-phenylbutyliden)-9(10H)-anthracenone (III) was prepared from IIII as described above, and gave 5 yellow crystals (0.30 g, 65%); mp 84–86° C.; $^1$H-NMR (CDCl$_3$) δ 12.45 (s, 1H), 12.30 (s, 1H), 7.65-6.90 (m, 11H), 6.55 (t, 1H, J=7.4 Hz), 2.85-2.50 (m, 4H), 2.15-1.75 (m, 2H); FTIR 1630 cm$^{-1}$ (CO . . . OH); UV (CH$_2$Cl$_2$) λ$_{max}$ (log ε) 383 (4.12), 296 (4.10), 233 nm (4.60). Anal. (C$_{24}$H$_{20}$O$_3$) C, H.

1,8-Dihydroxy-10-(5-phenylpentyliden)-9(10H)-anthracenone (IIm) was prepared from IIIm as described above. Recrystallization from methanol gave yellow crystals (0.25 g, 54%); mp 40° C.; $^1$H-NMR (CDCl$_3$) δ 12.40 (s, 1H), 12.25 (s, 1H), 7.70-6.85 (m, 11H), 6.55 (t, 1H, J=7.4 Hz), 2.80-2.50 (m, 4H), 1.90-1.50 (m, 2H); FTIR 1630 cm$^{-1}$ (CO . . . OH); UV (CH$_2$Cl$_2$) $\lambda_{max}$ (log ε) 383 (4.09), 295 (4.07), 239 nm (4.39); MS m/z 370 (81%). Anal. (C$_{25}$H$_{22}$O$_3$) C, H.

1,8-Dihydroxy-10-(2-phenylethyliden)-9(10H)-anthracenone (IIi). A suspension of IIIi (0.5 g, 1.39 mmol) in absolute methanol (10 ml) was treated with DBU (1.1 g, 7.23 mmol). The reaction was terminated exactly after 3 min by addition of excess 6N HCl. The reaction mixture was shaken thoroughly and extracted with CH$_2$Cl$_2$. The organic phase was dried over Na$_2$SO$_4$ and then evaporated. The residue was purified by chromatography using CH$_2$Cl$_2$ as eluant. The concentrated crude product was treated with a small amount of hexane to induce precipitation of IIi as yellow crystals (0.25 g, 55%, 97% isomerically pure by HPLC analysis); mp 128–129° C.; $^1$H-NMR (250 MHz, CDCl$_3$) δ 12.37 (s, 1H), 12.22 (s, 1H), 7.65-6.90 (m, 11H), 6.68 (t, 1H, J=7.4 Hz), 3.95 (d, 2H, J=7.4 Hz); FTIR 1630 cm$^{-1}$ (CO . . . OH); UV (CH$_2$Cl$_2$) $\lambda_{max}$ (log ε) 384 (4.11), 295 (4.09), 233 nm (4.61); MS m/z 328 (74%). Anal. (C$_{22}$H$_{16}$O$_3$) C, H.

10-(4-Carboxyphenylmethylene)-1,8-dihydroxy-9(10H)-anthracenone (IIn). A suspension of IIe (0.5 g, 1.47 mmol) in 50% sulfuric acid (40 ml) and glacial acetic acid (40 ml) was refluxed for 24 h. The reaction mixture was cooled in an ice bath and the resulting crystals were filtered by suction, washed thoroughly with water, then with a small amount of cold methanol and then with petroleum ether (40–60) to afford a yellow powder (0.42 g, 85%); mp 280° C. (decomposition); $^1$H-NMR (DMSO-d$_6$) δ 12.10 (s, 1H), 12.00 (s, 1H), 7.95–6.85 (m, 11H); FTIR 1681 (COOH), 1630 cm$^{-1}$ (CO . . . OH); UV (MeOH) $\lambda_{max}$ (log ε) 396 (4.12), 278 (4.24), 235 nm (4.67); MS m/z 358 (82%). Anal. (C$_{22}$H$_{14}$O$_5$) C, H.

1,8-Dihydroxy-10-[(4-methoxycarbonyl)phenylmethylen)-9(10H)-anthracenone (IIo). A suspension of IIn (0.5 g, 1.40 mmol) in absolute methanol (160 ml) and 96% sulfuric acid (0.5 ml) was refluxed for 24 h. The reaction mixture was cooled to -20° C. and the resulting crystals were filtered by suction. Purification by chromatography using CH$_2$Cl$_2$ as eluant gave orange-yellow crystals (0.28 g, 58%); mp 167–168° C.; $^1$H-NMR (CDCl$_3$) δ 12.30 (s, 1H), 12.20 (s, 1H), 8.10-6.90 (m, 11H), 3.95 (s, 3H); FTIR 1717 (CO$_2$CH$_3$), 1630 cm$^{-1}$ (CO . . . OH); UV (MeOH) $\lambda_{max}$ (log ε) 397 (4.14), 305 (4.24), 234 nm (4.68); MS m/z 372 (80%). Anal. (C$_{23}$H$_{16}$O$_5$) C, H.

1,8-Dihydroxy-10-[(4-hydroxyphenyl)methylen]-9(10H)-anthracenone (IIp). A solution of IIf (0.5 g, 1.45 mmol) in dry CH$_2$Cl$_2$ (10 ml) was added dropwise to a solution of BBr$_3$ (0.72 ml, 7.26 mmol) in CH$_2$Cl$_2$ (20 ml) at -70° C. The mixture was allowed to warm to room temperature and stirred for 24 h. Excess water was added and the mixture was extracted with ether. The ether phase was dried and evaporated, and the residue purified by chromatography using CH$_2$Cl$_2$/ether (9+1). The concentrated crude product was treated with a small amount of hexane to induce precipitation of IIp as orange-red crystals (0.33 g, 69%); mp 220–221° C.; $^1$H-NMR (DMSO-d$_6$) δ 12.15 (s, 1H), 12.00 (s, 1H), 9.80 (s, 1H), 7.70-6.60 (m, 11H); FTIR 3423 (OH), 1630 cm$^{-1}$ (CO . . . OH); UV (MeOH) $\lambda_{max}$ (log ε) 452 (3.98), 390 (4.05), 340 (3.98), 283 (4.04), 239 nm (4.59); MS m/z 330 (100%). Anal. (C$_{21}$H$_{14}$O$_4$) C, H.

1,8-Dihydroxy-10-[(3,4-dihydroxyphenyl)methylen]-9(10H)-anthracenone (IIq) was prepared from IIg according to the method described for IIp and provided IIq as orange-red crystals (0.32 g, 78%); mp 216° C.; $^1$H-NMR (DMSO-d$_6$) δ 12.25 (s, 1H), 12.10 (s, 1H), 9.40 (s, 1H), 9.10 (s, 1H), 7.80-6.75 (m, 10H); FTIR 3377 (OH), 1630 cm$^{-1}$ (CO . . . OH); UV (MeOH) $\lambda_{max}$ (log ε) 460 (3.92), 391 (4.00), 288 (4.08), 239 nm (4.51); MS m/z 346 (100%). Anal. (C$_{21}$H$_{14}$O$_5$) C, H.

1,8-Dihydroxy-10-[(3,4,5-trihydroxyphenyl)methylen]-9(10H)-anthracenone (IIr) was prepared from IIh according to the method described for IIp, and provided IIr as red crystals (0.27 g, 60%); mp 211–212° C.; $^1$H-NMR (DMSO-d$_6$) δ 12.30 (s, 1H), 12.10 (s, 1H), 9.00 (s, 2H), 8.50 (s, 1H), 7.80-6.80 (m, 7H), 6.40 (s, 2H); FTIR 3315 (OH), 1630 cm$^{-1}$ (CO . . . OH); UV (MeOH) $\lambda_{max}$ (log ε) 467 (3.89), 389 (3.98), 289 (4.06), 236 nm (4.49); MS m/z 362 (1%). Anal. (C$_{21}$H$_{14}$O$_6$) C, H.

Additional Experimental Details

EXAMPLE 7

Additional information applicable to confirming the results of the synthesis procedures of the invention (see results in Table III) is as follows.

All temperatures are in degrees centigrade. Melting points were determined with a Büchi 510 melting point apparatus and are uncorrected. Chromatography refers to column chromatography on silica gel (E. Merck, 70–230 mesh). $^1$H-NMR spectra were recorded with a Varian EM 390 (90 MHz) or a Bruker Spectrospin WM 250 (250 MHz); δ values are in ppm relative to a tetramethylsilane internal standard. Fourier-transform-IR spectra (KBr) were recorded on a Nicolet 510M FTIR spectrometer. Mass spectra (EI, 70 eV, unless otherwise stated) were obtained on a Varian MAT CH5, PI-FDMS on a Varian MAT 95.

log P Determinations

A standard reversed-phase HPLC method was used, Unger, S. H., et al., "Simple Procedure for Determining Octanol-Aqueous Partition, Distribution, and Ionization Coefficients by Reversed-Phase High-Pressure Liquid Chromatography, J. Pharm. Sci., 1978, 67:1364–1367; Terada, H., "Determination of Log P$_{oct}$ by High-Performance Liquid Chromatography, and Its Application in the Study of Quantitative Structure-Activity Relationships", Quant. Struct. Act. Relat., 1986, 5:81–88, for the determination of octanol-water partition coefficients of the compounds Ia–Iu and IIa–IIr. The results of these determinations are presented in Tables III.

The method is based on the linear relationship between the capacity factors log K' of the compounds and their log P values. The log k' values of five compounds (4-nitrophenol, 4-chlorophenol, benzophenone, naphthalene, and anthracene) with known log P values (1.91, 2.39, 3.81, 3.44, and 4.49, respectively) were determined. A plot of log K' versus log P generated from this calibration mixture was used for calculation of log P values for the new compounds from the logarithms of their capacity factors (correlation coefficient >0.99; n=3). HPLC: Nucleosil C$_{18}$; methanol/water/acetic acid (77+23+0.1), adjusted to pH 5.5 with conc. NH$_3$, was used as eluant.

EXAMPLE 8

An especially preferred compound of formula I is 1,8-dihydroxy-10-[2-(4-methylphenyl)-1-oxoethyl]-9(10H)-anthracenone (Compound Iv). Compound Iv was prepared and tested as follows.

Experimental protocol: Melting points, column chromatography, $^1$H-NMR spectra, and IR spectra are as set forth hereinabove in Example 7. Mass spectra (EI) were obtained on a Varian MAT 112S spectrometer (EI-MS, 70 eV). Elemental analyses indicatd by the symbols of the elements were within ±0.4% of theoretical values. HPLC (Kontron 420, 735 LC UV detector) was performed on a 250×4-mm column (4-x 4-mm precolumn) packed with LiChrospher 100 RP18 (5-μm particles; Merck, Darmstadt, Germany). Data were recorded on a MacLab data acquisition system (WissTech, Germany) and analysis was performed with the software peaks on an Apple Macintosh computer.

Compound Iv was obtained from a reaction between anthralin and 4-methylphenylacetic acid (commercially available from Aldrich). Specifically, to a solution of anthralin (1.00 g, 4.42 mmol) (prepared in accordance with Auterhoff et al, *Arch. Pharm., supra*), 4-methylphenylacetic acid (0.80 g, 5.30 mmol) and dicyclohexylcarbodiimide (1.10 g, 5.30 mmol) in absolute THF (30 ml) was added dry pyridine (2.0 ml, 25.40 mmol) under $N_2$. The reaction mixture was stirred at room temperature for four hours, filtered, and the filtrate was evaporated. The residue was purified by column chromatography using $CH_2Cl_2$/hexane (8/2), and recrystallization from benzene/hexane (7/3) afforded yellow needles; 18% yield; mp 152–154° C.; FTIR 1711, 1630 $cm^{-1}$; $^1H$ NMR ($CDCl_3$) δ 12.26 (s, 2H), 7.54-6.59 (m, 10H), 5.31 (s, 1H), 3.33 (s, 2H), 2.26 (s, 3H). Anal $C_{23}H_{18}O_4$ (C,H).

The results of testing between compound Iv and anthralin are set forth in Table IV immediately below:

TABLE IV

| Compound | R | log P | AA $IC_{50}$ $(\mu M)^a$ | LDH $(mU)^b$ | 5-LO $IC_{50}(\mu M)^c$ | $DD(OH)^d$ |
|---|---|---|---|---|---|---|
| anthralin | | 4.23 | 0.7 | 294 | 37 | $2.89 \pm 0.14^e$ |
| Iv | 4-Methyl | 4.54 | 0.7 | $145^f$ | 0.6 | <0.3 |

$^a$Antiproliferative activity against HaCaT cells. Inhibition of cell growth was significantly different with respect to that of the control, N = 3, P < 0.01.
$^b$Activity of LDH (mU) release in HaCaT cells after treatment with 2 μM test compound (N = 3, SD < 10%).
$^c$Inhibition of 5-HETE and $LTB_4$ biosynthesis in bovine PMNL. Inhibition was significantly different with respect to that of the control; N = 3 or more, P < 0.01. Nordihydroguaiaretic acid (NDGA) was used as the standard inhibitor for 5-LO ($IC_{50}$ = 0.4 μM).
$^d$Deoxyribose degradation as a measure of hydroxyl-radical formation. Indicated values are μmol of malondialdehyde/mmol of deoxyribose released by 75 μm test compound.
$^e$Values are significantly different with respect to vehicle control.
$^f$Values are not significantly different with respect to vehicle control.

The biological assay methods were as follows: LDH release as described in Muller K, Huang H-S, Wiegrebe W, *J. Med. Chem.* 39, 3132–3138 (1996); bovine PMNL 5-LO assay as described in Muller K, Gurster D, Piwek S, Wiegrebe W, *J. Med. Chem.* 36, 4099–4107 (1993); and degradation of 2-deoxy-D-ribose as described in Muller K, Gurster D, *Biochem. Pharmacol.* 46, 1695–1704 (1993). HaCaT keratinocyte proliferation assay was generally described in Muller K, Leukel P, Zeireis K, Gawlik I, *J. Med. Chem* 37, 1660–1669 (1994). Specifically, the HaCaT cells were incubated with the test compounds (2 microM) for four hours at 37° C. Extracellular LDH activity was measured using the UV method with pyruvate and NADH and is expressly in mU/ml. Appropriate controls with the vehicle were performed (P<0.01; N=3, SD<10%).

Log P was determined by a standard reversed-phase HPLC procedure as described in Unger S H, Cook J R, Hollenberg J S, *J. Pharm. Sci.* 67, 1364–1367 (1978). MeOH/water/HOAc (77/23/0.1), adjusted to pH 5.5 with concentrated $NH_3$, was used as eluant. Calibration was performed as described in Muller K, Gurster D, Piwek S, Wiegrebe W, *J. Med. Chem.* 36, 4099–4107 (1993).

Lactate Dehydrogenase Release

A major concern in the testing of potential inhibitors of cell growth is to confirm that the drug does not interfere with the functioning of cell membranes by causing leakage of cytoplasm through it. Anthralin has been reported to cause membrane damage, but did not directly lead to substantial membrane destruction (Bonnekoh, B.; Farkas, B.; Geisel J.; Mahrle, G. "Lactate dehydrogenase release as an indicator of dithranol-induced membrane injury in cultured human keratinocytes", *Arch. Dermatol. Res.*, 282, 325–329 (1990)). Cytotoxicity against cell cultures by the potent cell growth inhibitors was assessed by the activity of lactate dehydrogenase (LDH) activity release into the culture medium. The release of LDH is commonly used as an indicator of plasma membrane damage. In this assay, LDH release by anthralin significantly exceeded that of the vehicle control. On the other hand, the LDH release of compound Iv was not significantly different as compared to vehicle controls.

EXAMPLE 9

An especially preferred compound of formula I is (R,S)-1,8-dihydroxy-10-(1-oxo-4-phenylpentyl)-9(10H)-anthracenone(Compound Iw). Compound Iw was prepared and tested as follows.

The experimental protocol utilized in this testing is described in Example 8.

Compound Iw was obtained as follows. To a solution of anthralin (1.00 g, 4.42 mmol) (prepared in accordance with Auterhoff et al, *Arch. Pharm., supra*) in absolute toluene (75 ml) and dry pyridine (0.43 ml, 5.50 mmol) was added dropwise a solution of (R,S)-4-phenylvaleryl chloride (5.50 mmol)in absolute toluene (10 ml) under $N_2$. The reaction mixture was stirred at room temperature for 12 hours, filtered, and the filtrate was evaporated. Purification by column chromatography using $CH_2Cl_2$/hexane (3/2) gave a yellow powder; 33% yield; mp 82° C.; FTIR 1711, 1628 $cm^{-1}$; $^1H$ NMR ($CDCl_3$) δ 12.19 (s, 2H), 7.57-6.76 (m, 11H), 5.12 (s, 1H), 2.55-2.17 (m,1H), 1.97-1.42(m,4H), 1.02 (d,J=7 Hz, 3H); MS m/z=386 (5,$M^+$), 226 (100). Anal $C_{25}H_{22}O_4$ (C,H).

The results of testing between compound Iw and anthralin are set forth in Table V immediately below:

TABLE V

| Compound | X | R | AA $IC_{50}$ $(\mu M)^a$ | LDH $(mU)^b$ | 5-LO $IC_{50}$ $IC_{50}$ $(\mu M)^c$ | DD $(OH)^d$ |
|---|---|---|---|---|---|---|
| Anthralin | | | 0.7 | 294 | 37 | $2.89 \pm 0.14^e$ |
| Iw | $(CH_2)_2$ $(CH_3)CH$ (R, S) | H | 0.8 | 171 | 0.3 | <0.3 |

$^{abcde}$Same as in Example 8.

What is claimed is:

1. A compound consisting of 1,8-dihydroxy-10-[2-(4-methylphenyl)-1-oxoethyl]-9(10H)-anthracenone.

2. A pharmaceutical composition for treatment of inflammatory conditions comprising a therapeutically effective amount of 1,8-dihydroxy-10-[2-(4-methylphenyl)-1-oxoethyl]-9(10H)-anthracenone and a pharmaceutically acceptable carrier.

3. The pharmaceutical composition of claim 2, wherein said inflammatory condition is psoriasis.

4. A method for treating inflammatory conditions comprising administering to a patient exhibiting such inflammatory conditions a pharmaceutical composition comprising a therapeutically effective amount of 1,8-dihydroxy-10-[2-(4-methylphenyl)-1-oxoethyl]-9(10H)-anthracenone and a pharmaceutically acceptable carrier.

5. The method of claim 4, wherein said inflammatory condition is psoriasis.

6. A compound consisting of (R,S)-1,8-dihydroxy-10-(1-oxo-4-phenylpentyl)-9(10H)-anthracenone.

7. A pharmaceutical composition for treatment of inflammatory conditions comprising a therapeutically effective amount of (R,S)-1,8-dihydroxy-10-(1-oxo-4-phenylpentyl)-9(10H)-anthracenone and a pharmaceutically acceptable carrier.

8. The pharmaceutcial composition of claim 7, wherein said inflammatory condition is psoriasis.

9. A method for treating inflammatory conditions comprising administering to a patient exhibiting such inflammatory conditions a pharmaceutical composition comprising a therapeutically effective amount of (R,S)-1,8-dihydroxy-10-(1-oxo-4-phenylpentyl)-9(10H)-anthracenone and a pharmaceutically acceptable carrier.

10. The method of claim 9, wherein said inflammatory condition is psoriasis.

\* \* \* \* \*